(12) United States Patent
Wen et al.

(10) Patent No.: US 9,939,999 B2
(45) Date of Patent: Apr. 10, 2018

(54) TREATMENT OF TEETH BY ALIGNERS

(71) Applicant: Align Technology, Inc., San Jose, CA (US)

(72) Inventors: Huafeng Wen, Redwood City, CA (US); Frank Zhenhuan Liu, San Carlos, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 567 days.

(21) Appl. No.: 14/255,832

(22) Filed: Apr. 17, 2014

(65) Prior Publication Data

US 2014/0229878 A1     Aug. 14, 2014

Related U.S. Application Data

(60) Continuation of application No. 12/511,943, filed on Jul. 29, 2009, now Pat. No. 8,740,614, which is a
(Continued)

(51) Int. Cl.
    *A61C 7/00*     (2006.01)
    *G06F 3/0484*     (2013.01)
    (Continued)

(52) U.S. Cl.
    CPC .............. *G06F 3/0484* (2013.01); *A61C 7/00* (2013.01); *A61C 7/002* (2013.01); *A61C 7/08* (2013.01);
(Continued)

(58) Field of Classification Search
    CPC ....... A61C 7/00–7/0036; A61C 9/0002; A61C 13/0004; A61C 2007/004; G06F 3/0484; B33Y 80/00
(Continued)

(56) References Cited

U.S. PATENT DOCUMENTS

| 1,813,583 A | 7/1931 | Rice |
| 2,037,344 A | 4/1936 | Schwartz |

(Continued)

FOREIGN PATENT DOCUMENTS

| AU | 3031677 A | 5/1979 |
| AU | 517102 B2 | 7/1981 |

(Continued)

OTHER PUBLICATIONS

Partial International European Search Report for Application # 06750215.3, 7 pages, mailed Jan. 5, 2015 (Jan. 5, 2015).
(Continued)

*Primary Examiner* — Yogesh Patel
(74) *Attorney, Agent, or Firm* — Wilson Sonsini Goodrich & Rosati

(57) ABSTRACT

A method for treating a subject's teeth. A target configuration for the subject's teeth is determined. Receiving features are produced on a dental base in response to the target configuration, the receiving features being configured to receive physical tooth models. The physical tooth models are assembled on the dental base to form a physical arch model. A dental aligner is produced using the physical arch model to move the subject's teeth to the target configuration.

10 Claims, 11 Drawing Sheets

Related U.S. Application Data division of application No. 11/404,332, filed on Apr. 13, 2006, now abandoned.

(60) Provisional application No. 60/676,278, filed on Apr. 29, 2005.

(51) Int. Cl.
*A61C 7/08* (2006.01)
*B33Y 80/00* (2015.01)
*A61C 9/00* (2006.01)
*A61C 13/00* (2006.01)

(52) U.S. Cl.
CPC .......... *A61C 9/002* (2013.01); *A61C 13/0004* (2013.01); *A61C 2007/004* (2013.01); *B33Y 80/00* (2014.12)

(58) Field of Classification Search
USPC ...................................................... 433/3–24
See application file for complete search history.

(56) References Cited

U.S. PATENT DOCUMENTS

| | | |
|---|---|---|
| 2,138,254 A | 11/1938 | Mink |
| 2,467,432 A | 4/1949 | Kesling |
| 2,700,218 A | 1/1955 | Lindley |
| 3,218,711 A | 11/1965 | Connan |
| 3,407,500 A | 10/1968 | Kesling |
| 3,436,829 A | 4/1969 | Jermyn |
| 3,453,736 A | 7/1969 | Waltke |
| 3,470,614 A | 10/1969 | Kelly |
| 3,576,075 A | 4/1971 | Scott |
| 3,600,808 A | 8/1971 | James |
| 3,660,900 A | 5/1972 | Andrews |
| 3,683,502 A | 8/1972 | Melvin |
| 3,702,027 A | 11/1972 | Marshall et al. |
| 3,738,005 A | 6/1973 | Cohen et al. |
| 3,760,503 A | 9/1973 | Baskas |
| 3,860,803 A | 1/1975 | Levine |
| 3,890,710 A | 6/1975 | Jaeger |
| 3,905,106 A | 9/1975 | Costa et al. |
| 3,916,526 A | 11/1975 | Schudy |
| 3,922,786 A | 12/1975 | Lavin |
| 3,932,939 A | 1/1976 | Weissman |
| 3,937,773 A | 2/1976 | Huffman |
| 3,950,851 A | 4/1976 | Bergersen |
| 3,983,628 A | 10/1976 | Acevedo |
| 4,014,096 A | 3/1977 | Dellinger |
| 4,122,606 A | 10/1978 | Roman |
| 4,173,505 A | 11/1979 | Jacobs |
| 4,195,046 A | 3/1980 | Kesling |
| 4,203,219 A | 5/1980 | Wiener |
| 4,253,828 A | 3/1981 | Coles et al. |
| 4,265,619 A | 5/1981 | Lucki et al. |
| 4,324,546 A | 4/1982 | Heitlinger et al. |
| 4,324,547 A | 4/1982 | Arcan et al. |
| 4,348,178 A | 9/1982 | Kurz |
| 4,368,042 A | 1/1983 | Felstead et al. |
| 4,374,076 A | 2/1983 | Stephan et al. |
| 4,475,888 A | 10/1984 | Gores et al. |
| 4,478,580 A | 10/1984 | Barrut |
| 4,494,934 A | 1/1985 | Huffman |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,529,384 A | 7/1985 | Severy |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,657,992 A | 4/1987 | Brennan et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,767,330 A | 8/1988 | Burger |
| 4,793,803 A | 12/1988 | Martz |
| 4,798,534 A | 1/1989 | Breads |
| 4,828,117 A | 5/1989 | Panzera et al. |
| 4,834,651 A | 5/1989 | Fenick |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,943,237 A | 7/1990 | Bryan |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andersson et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,466,152 A | 11/1995 | Walter |
| 5,474,448 A | 12/1995 | Andreiko et al. |
| RE35,169 E | 3/1996 | Lemchen et al. |
| 5,518,397 A | 5/1996 | Andreiko et al. |
| RE35,263 E | 6/1996 | Silva et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,616,899 A | 4/1997 | Recigno |
| 5,618,176 A | 4/1997 | Andreiko et al. |

(56) References Cited

U.S. PATENT DOCUMENTS

| | | |
|---|---|---|
| 5,621,648 A | 4/1997 | Crump |
| 5,645,420 A | 7/1997 | Bergersen |
| 5,645,421 A | 7/1997 | Slootsky |
| 5,647,744 A | 7/1997 | Squicciarini |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,788,489 A | 8/1998 | Huffman |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,911,580 A | 6/1999 | Sharp et al. |
| 5,927,984 A | 7/1999 | Lin |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,326 B1 | 4/2001 | Hahn |
| 6,217,334 B1 | 4/2001 | Hultgren |
| 6,227,850 B1 | 5/2001 | Chishti et al. |
| 6,227,851 B1 | 5/2001 | Chishti et al. |
| 6,244,861 B1 | 6/2001 | Andreiko et al. |
| 6,261,098 B1 | 7/2001 | Persson |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,386,865 B1 | 5/2002 | Suh et al. |
| 6,398,548 B1 | 6/2002 | Muhammad et al. |
| 6,402,707 B1 | 6/2002 | Ernst |
| 6,423,252 B1 | 7/2002 | Chun et al. |
| 6,425,759 B1 | 7/2002 | Cronin |
| 6,471,511 B1 | 10/2002 | Chishti et al. |
| 6,482,298 B1 | 11/2002 | Bhatnagar |
| 6,497,574 B1 | 12/2002 | Miller |
| 6,499,997 B2 | 12/2002 | Chishti et al. |
| 6,524,101 B1 | 2/2003 | Phan et al. |
| 6,541,074 B2 | 4/2003 | Cho |
| 6,554,611 B2 | 4/2003 | Chishti et al. |
| 6,572,372 B1 | 6/2003 | Phan et al. |
| 6,582,227 B2 | 6/2003 | Phan et al. |
| 6,582,229 B1 | 6/2003 | Miller et al. |
| 6,602,070 B2 | 8/2003 | Miller et al. |
| 6,607,382 B1 | 8/2003 | Kuo et al. |
| 6,621,491 B1 | 9/2003 | Baumrind et al. |
| 6,626,666 B2 | 9/2003 | Chishti et al. |
| 6,626,669 B2 | 9/2003 | Zegarelli |
| 6,629,840 B2 | 10/2003 | Chishti et al. |
| 6,633,789 B1 | 10/2003 | Nikolskiy et al. |
| 6,665,570 B2 | 12/2003 | Pavloskaia et al. |
| 6,682,346 B2 | 1/2004 | Chishti et al. |
| 6,685,469 B2 | 2/2004 | Chishti et al. |
| 6,685,470 B2 | 2/2004 | Chishti et al. |
| 6,688,886 B2 | 2/2004 | Hughes et al. |
| 6,699,037 B2 | 3/2004 | Chishti et al. |
| 6,705,861 B2 | 3/2004 | Chishti et al. |
| 6,705,863 B2 | 3/2004 | Phan et al. |
| 6,722,880 B2 | 4/2004 | Chishti et al. |
| 6,726,478 B1 | 4/2004 | Isiderio et al. |
| 6,729,876 B2 | 5/2004 | Chishti et al. |
| 6,846,179 B2 | 1/2005 | Chapouland et al. |
| 6,882,894 B2 | 4/2005 | Durbin et al. |
| 6,884,068 B2 | 4/2005 | Huffman |
| 6,913,462 B2 | 7/2005 | Honstein et al. |
| 6,923,649 B2 | 8/2005 | Oswald et al. |
| 6,981,874 B2 | 1/2006 | Allred et al. |
| 7,040,897 B2 | 5/2006 | Fischer |
| 7,048,031 B2 | 5/2006 | Usui |
| 7,153,135 B1 | 12/2006 | Thomas |
| 7,156,655 B2 | 1/2007 | Sachdeva et al. |
| 7,186,760 B2 | 3/2007 | Rudo |
| 7,250,611 B2 | 7/2007 | Aguirre et al. |
| 7,384,266 B2 | 6/2008 | Wen |
| 7,435,083 B2 | 10/2008 | Chishti et al. |
| 7,435,084 B2 | 10/2008 | Liu et al. |
| 8,740,614 B2 | 6/2014 | Wen et al. |
| 2001/0002310 A1* | 5/2001 | Chishti ............... A61C 7/00 433/24 |
| 2001/0027401 A1 | 10/2001 | Klein |
| 2001/0037248 A1 | 11/2001 | Klein |
| 2002/0006597 A1 | 1/2002 | Andreiko et al. |
| 2002/0015934 A1 | 2/2002 | Rubbert et al. |
| 2002/0017998 A1 | 2/2002 | Price |
| 2002/0064747 A1* | 5/2002 | Chishti ............... A61C 7/00 433/24 |
| 2002/0094503 A1 | 7/2002 | Chishti et al. |
| 2002/0150855 A1 | 10/2002 | Chishti et al. |
| 2002/0187451 A1 | 12/2002 | Phan et al. |
| 2003/0002089 A1 | 1/2003 | Vadnais et al. |
| 2003/0003416 A1 | 1/2003 | Chishti et al. |
| 2003/0009252 A1 | 1/2003 | Pavlovskaia et al. |
| 2003/0039940 A1 | 2/2003 | Miller |
| 2003/0139834 A1 | 7/2003 | Nikolskiy et al. |
| 2003/0203334 A1 | 10/2003 | Hedge et al. |
| 2003/0207227 A1 | 11/2003 | Abolfathi |
| 2003/0224311 A1 | 12/2003 | Cronauer |
| 2004/0023185 A1 | 2/2004 | Gittleman |
| 2004/0063060 A1 | 4/2004 | Meyers et al. |
| 2004/0109783 A1 | 6/2004 | Prasad et al. |
| 2004/0115587 A1 | 6/2004 | Breining et al. |
| 2004/0128010 A1 | 7/2004 | Pavlovskaia et al. |
| 2004/0197727 A1* | 10/2004 | Sachdeva ........... A61C 7/00 433/24 |
| 2004/0197728 A1 | 10/2004 | Abolfathi et al. |
| 2004/0234929 A1 | 11/2004 | Fischer et al. |
| 2005/0003319 A1 | 1/2005 | Kuo |
| 2005/0055118 A1 | 3/2005 | Nikolskiy et al. |
| 2005/0186150 A1 | 8/2005 | Allred |
| 2005/0186526 A1 | 8/2005 | Stewart et al. |
| 2006/0093982 A1 | 5/2006 | Wen |
| 2006/0093987 A1 | 5/2006 | Wen |
| 2006/0093992 A1 | 5/2006 | Wen |
| 2006/0093993 A1 | 5/2006 | Wen |
| 2006/0127838 A1 | 6/2006 | Liu et al. |
| 2006/0127850 A1 | 6/2006 | Wen |
| 2006/0127851 A1 | 6/2006 | Wen |
| 2006/0127857 A1 | 6/2006 | Zhenhuan et al. |
| 2006/0127858 A1 | 6/2006 | Wen |
| 2006/0127860 A1 | 6/2006 | Wen |
| 2006/0134580 A1 | 6/2006 | Raby et al. |
| 2006/0275731 A1 | 12/2006 | Wen et al. |
| 2006/0275736 A1 | 12/2006 | Wen et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |

(56) References Cited

FOREIGN PATENT DOCUMENTS

| | | |
|---|---|---|
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1876993 A2 | 1/2008 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | 2006115841 A2 | 11/2006 |

OTHER PUBLICATIONS

Kuroda, et al., "Three-dimensional dental cast analyzing system using laser scanning", American Journal Orthod. Dentofac.Orthop. vol. 110, Oct. 1996, 365-369.

AADR. American Association for Dental Research, Summary of Activities, Mar. 20-23, 1980, Los Angeles, CA, p. 195.

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty, NATO Symposium on Applications of Human Biostereometrics," Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. In Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form in Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

Cardinal Industrial Finishes, Powder Coatings information posted at< http://www.cardinalpaint.com> on Aug. 25, 2000, 2 pages.

Carnaghan, "An Alternative to Holograms for the Portrayal of Human Teeth," 4th Int'l Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside," Part 2 F. Duret—A Man with a Vision, "Part 3 the Computer Gives New Vision—Literally," Part 4 Bytes 'N Bites—The Computer Moves from the Front Desk to the Operatory, Canadian Dental Journal, vol. 54 (9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

(56) References Cited

OTHER PUBLICATIONS

Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98-Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstress putonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).

(56) References Cited

OTHER PUBLICATIONS

Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Pat. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).

(56) References Cited

OTHER PUBLICATIONS

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances-Pro Lab product information for patients, 2 pages (2002).

\* cited by examiner

TREATMENT OF TEETH BY ALIGNERS

CROSS-REFERENCES TO RELATED INVENTIONS

This application is a continuation and claims priority to and benefit of U.S. patent application Ser. No. 12/511,943, filed on Jul. 29, 2009, now U.S. Pat. No. 8,740,614, titled "Treatment of Teeth by Aligners" by Huafeng Wen, assigned to the assignee of the present application, which is herein incorporated by reference in its entirety.

The U.S. patent application Ser. No. 12/511,943 claims priority to the abandoned U.S. patent application Ser. No. 11/404,332, titled "Treatment of Teeth by Aligners" with the filing date of Apr. 13, 2006, which is herein incorporated by reference in its entirety. This application claims the benefit of U.S. Provisional Patent application 60/676,278, filed on Apr. 29, 2005, which is herein incorporated by reference in its entirety.

The U.S. patent application Ser. No. 12/511,943 is related to U.S. Provisional Patent Application No. 60/676,546, filed Apr. 29, 2005, titled "Digitization of dental arch model" by Huafeng Wen and U.S. patent application Ser. No. 11/205,496, filed Aug. 16, 2005, titled "System for organizing dental aligners" by Huafeng Wen, which are herein incorporated by reference in their entirety.

The U.S. patent application Ser. No. 12/511,943 is related to U.S. patent application Ser. No. 11/074,301, titled "Dental aligner for providing accurate dental treatment" by Liu et al, filed Mar. 7, 2005, U.S. patent application Ser. No. 11/074,297, titled "Producing wrinkled dental aligner for dental treatment" by Liu et al, filed Mar. 7, 2005, U.S. patent application Ser. No. 11/074,300, titled "Fluid permeable dental aligner" by Huafeng Wen, filed Mar. 7, 2005, U.S. patent application Ser. No. 11/074,298, titled "Disposable dental aligner" by Huafeng Wen, filed Mar. 7, 2005, and U.S. patent application Ser. No. 11/050,051, titled "Storage system for dental devices" by Huafeng Wen, filed Feb. 3, 2005, which are herein incorporated by reference in their entirety.

The U.S. patent application Ser. No. 12/511,943 is related to U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004, which are herein incorporated by reference in their entirety.

The U.S. patent application Ser. No. 12/511,943 is related to U.S. patent application Ser. No. 11/013,152, titled "A base for physical dental arch model" by Huafeng Wen, filed Dec. 14, 2004, U.S. patent application Ser. No. 11/012,924, titled "Accurately producing a base for physical dental arch model" by Huafeng Wen, filed Dec. 14, 2004, U.S. patent application Ser. No. 11/013,145, titled "Fabricating a base compatible with physical tooth models" by Huafeng Wen, filed Dec. 14, 2004, U.S. patent application Ser. No. 11/013,156, titled "Producing non-interfering tooth models on a base" by Frank Zhenhuan Liu et al, filed Dec. 14, 2004, U.S. patent application Ser. No. 11/013,160, titled "System and methods for casting physical tooth model" by Frank Zhenhuan Liu et al, filed Dec. 14, 2004, U.S. patent application Ser. No. 11/013,159, titled "Producing a base for accurately receiving dental tooth models" by Huafeng Wen, and filed Dec. 14, 2004, U.S. patent application Ser. No. 11/013,157, titled "Producing accurate base for dental arch model" by Huafeng Wen, filed Dec. 14, 2004, which are herein incorporated by reference in their entirety.

FIELD OF THE INVENTION

This application generally relates to the field of dental care, and more particularly to the field of orthodontics.

BACKGROUND

Orthodontics is the practice of manipulating a subject's teeth to provide better function and appearance. In general, brackets are bonded to a subject's teeth and coupled together with an arched wire. The combination of the brackets and wire provides a force on the teeth causing them to move. Once the teeth have moved to a desired location and are held in place for a certain period of time, the body adapts bone and tissue to maintain the teeth in the desired location. A subject may be fitted with a retainer to help keep the teeth in the desired location.

Orthodontists initially base their treatment on a mental image of the subject's physical orthodontic structure and a mental image of a desired physical orthodontic structure for the subject, which may be assisted by x-rays and/or models. Based on these mental images, the orthodontist relies on his/her expertise to place the brackets and/or bands on the teeth and to manually bend (i.e., shape) wire, such that a force is asserted on the teeth to reposition them into the desired physical orthodontic structure. As the teeth move towards the desired location, the orthodontist makes continual judgments as to the progress of the treatment, the next step in the treatment (e.g., new bend in the wire, reposition or replace brackets, head gear, etc.), and the success of the previous step.

In general, an orthodontist makes manual adjustments to the wire and/or replaces or repositions brackets based on his or her expert opinion. Unfortunately, in the oral environment, it is difficult for a human being to accurately develop a visual three-dimensional image of an orthodontic structure due to the limitations of human sight and the physical structure of a human mouth. In addition, it is difficult (if not impossible) to accurately estimate three-dimensional wire bends (with accuracy within a few degrees) and to manually apply such bends to a wire. Further, it is difficult (or impossible) to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the success and speed of the process being dependent on the orthodontist's motor skills and diagnostic expertise. As a result of multiple wire changes, cost and subject discomfort is increased. The quality of care may also vary greatly from orthodontist to orthodontist, as does the time to treat a subject.

The practice of orthodontics relies heavily on the expert opinions and judgments of the orthodontist. Many innovations have been developed to aid orthodontists and other medical professionals attempting to align teeth. For example, U.S. Pat. No. 5,518,397 to Andreiko, et. al. provides a method of forming an orthodontic brace. The method includes obtaining a model of a subject's teeth and a prescription of desired positioning of the teeth. The contour of the subject's teeth is determined from the model. Calculations of the contour and the desired positioning of the subject's teeth are made and custom brackets are then created for receiving an arch wire to form an orthodontic brace system. The device of U.S. Pat. No. 5,518,397 places an arched wire on the bracket in a progressive curvature in a horizontal plane and a substantially linear configuration in a vertical plane. The brackets are customized to provide three-dimensional movement of the teeth. U.S. Pat. No. 5,518,397 to Andreiko, et. al., and all of the patents and references referred to in this specification, are hereafter incorporated by reference in their entirety.

Other innovations relating to bracket and bracket placements have also been patented. For example, such patent innovations are disclosed in U.S. Pat. No. 5,618,716 entitled "Orthodontic Bracket and Ligature" (a method of ligating arch wires to brackets), U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth."

Kuroda et al. (1996) Am. J. Orthodontics 110:365-369 describes a method for laser scanning a plaster dental cast to produce a digital image of the cast. See also U.S. Pat. No. 5,605,459, and U.S. Pat. Nos. 5,533,895; 5,474,448; 5,454,717; 5,447,432; 5,431,562; 5,395,238; 5,368,478; and 5,139,419, assigned to Ormco Corporation, describing methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198, and U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

Realistic simulations of teeth position are extremely helpful to many orthodontic treatment processes. Orthodontists may use plaster models of the upper and lower arch, to create a set-up that may be manipulated to model the starting and finishing positions of teeth. Thus, the teeth may be modeled to help eliminate guesswork. Brackets may be bonded to each tooth model to show the orthodontist the geometry of the wire to run through the bracket slots to achieve a desired result. The bracket position may then be transferred to the original malocclusion model. To make sure that the brackets will be bonded at exactly this position at the real subject's teeth, small templates for every tooth can be fabricated that fit over the bracket and a relevant part of the tooth and allow for reliable placement of the bracket on the subject's teeth. Alternatively, a transfer tray may be fabricated for each arch by placing each single bracket onto a model of the malocclusion and then fabricating a single transfer tray per arch that covers all brackets and relevant portions of every tooth. Thus, a transfer tray may help assure a very quick and yet precise bonding using indirect bonding.

U.S. Pat. No. 5,431,562 to Andreiko et al. describes a computerized, appliance-driven approach to orthodontics in which shape information of teeth is acquired and a target archform is calculated from the shape information. The shape of customized bracket slots, the bracket base, and the shape of the orthodontic archwire, are calculated in accordance with a mathematically-derived target archform. However, the orthodontist does not substantially interact with the appliance design.

Align Technologies also offers transparent, removable aligning devices. In this system, an orthodontist obtains an impression model of a subject's dentition and ships this model to a remote appliance manufacturing center, where it is scanned with a CT scanner. A computer model of the dentition in a final target situation is generated at the appliance manufacturing center and made available for viewing to the orthodontist over the Internet. The orthodontist indicates changes he or she wishes to make to individual tooth positions. Later, another virtual model is provided over the Internet and the orthodontist may review the revised model, and indicates any further changes. After several such iterations, the target situation is agreed upon. A series of removable aligning devices (or shells) are then manufactured and delivered to the orthodontist. The shells, in theory, will move the subject's teeth to the desired or (final) target position.

The coordination of the different steps of the treatment (the overall treatment process) typically involves early input from the practitioner (e.g., doctor, dental technician, etc.) in forming the aligner design referencing only the initial dental alignment of the subject. Most treatment processes do dynamically react to the ongoing treatment of the patent by the dental aligner. Thus, it may be difficult to optimize the interaction between the practitioner and the ongoing aligners produced.

U.S. Pat. No. 6,699,037 by Align Technology describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of at least three successive steps. The individual appliances preferably comprise a polymeric shell having the teeth-receiving cavity formed therein, typically by stereo lithographic molding. Each individual appliance is configured so that its tooth-receiving cavity has a geometry corresponding to an intermediate or end tooth arrangement intended for that appliance. That is, when an appliance is first worn by the subject, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

U.S. Pat. Nos. 6,471,511 and 6,682,346 describe Align Technology's stereo lithographic fabrication process. Several drawbacks exist however with the stereo lithography process. The materials used by stereo lithography processes may be toxic and harmful to human health. Stereo lithography builds the aligner layer by layer, which may create spaces susceptible to the growth of germs and bacteria when it is worn by a subject. Furthermore, Align Technology's stereo lithography process also requires a different aligner mold at each stage of the treatment, which produces a lot of waste and is environmental unfriendly. Thus, there is a need for practical, effective and efficient methods to produce a dental aligner.

Modeling a subject's teeth, such as modeling the upper or lower dental arches (including the manner in which the teeth interact) may be an important feature in using and creating an alignment device. A model of the subject's teeth can help guide the desired movement of the subject's teeth during an orthodontic treatment. The model can help avoid interference between a subject's teeth when undergoing dental re-alignment. A model can also provide input for the design and manufacturing of dental aligner devices. Thus, there is a need to accurately and efficiently obtain models of subjects' dental arches, including both virtual and actual models.

Another challenge for orthodontic treatment using aligning devices is to accurately translate the subject's teeth movement into treatment measures in the iterative treatment progress. The current treatment techniques are not able to quantitatively monitor the teeth movement of the subject's teeth and precisely adjust the treatment in accordance to the teeth movement of the subject's teeth.

Another challenge for orthodontic treatment using removable aligning devices is to accurately and most effectively render teeth movement. The current treatment techniques are often unable to account for the real and least resistance movement of the subject's teeth, which results in wanted teeth movement and/or unnecessary number of treatment steps.

By tracking the relative positions of the teeth in the upper and lower arches, dental aligner devices can be designed and fabricated to reflect the ongoing treatment by an orthodontist or user, as well as the effect of the treatment on the subject. This may ultimately save in cost, treatment time, and may also enhance user comfort.

Finally, the dental treatment processes may be designed to allow modification of the treatment steps based on the movement of the subject's teeth. Furthermore, there is a need for more optimal treatment processes, including the manufacturing of the dental aligners. Described herein are devices, systems, and methods which may address some of the problems described above.

SUMMARY OF THE INVENTION

The present invention provides methods, systems, and apparatus to design, manufacture and use dental alignment devices based on a subject's dental arches. Implementations of the methods, devices and systems described herein may include one or more of the following.

Generally described herein are methods of moving a subject's teeth (e.g., treating a subject) in which one or more aligners is provided to a subject to wear, so that the aligners may exert force to move the subject's teeth. The aligners may be designed as part of a series of aligners to be worn. The series may be determined based on the subject's initial teeth position, and based on input from a user (e.g., a practitioner such as a doctor, orthodontist, technician, etc.). In some variations, the treatment series (and therefore the aligners) may be designed based on feedback from the subject's teeth position as one or more of the aligners is worn. In some variations, the user may modify the series during treatment. In some variations, the series is determined based on one or more constrained directions of motion (e.g., in a translational direction or a rotational direction of an individual tooth). Specific variations and examples of the devices, methods and systems are provided.

Described herein are methods for producing a dental aligner to move a subject's teeth. In general, these methods may include the steps of: producing a tooth model simulating the tooth body of one of the subject's teeth, affixing to the tooth model one or more registration features simulating the roots of the subject's tooth, producing a dental base having one or more receiving features configured to receive the tooth model, and fabricating a dental aligner using the tooth model attached to the one or more receiving features on the dental base.

The step of fabricating a dental aligner may include producing a plurality of tooth models simulating the tooth bodies of the subject's teeth, assembling the physical tooth models on the dental base to form a physical arch model, and fabricating the dental aligner using the physical arch model attached to the dental base. The registration features on the physical tooth model may comprise pins or protrusions, and the receiving features may comprise sockets, slots or holes. The receiving features generally mate with the registration features. In some variations included herein, the receiving features may comprise pins or protrusions, and the registration features may comprise sockets, slots or holes. Any appropriate registration features and receiving features may be used.

A tooth model may be produced by producing a physical arch model of the subject's teeth using an impression of the subject's teeth, and separating the physical arch model into one or more tooth models. A dental aligner may be fabricated by vacuum forming the dental aligner using a sheet of aligner-making material over the tooth model attached to the dental base, or by CNC manufacture, or by casting.

Also described herein are systems for moving a subject's teeth, which may include a plurality of physical teeth models each having one or more registration features (wherein the registration features simulate the roots of the subject's teeth and wherein each tooth model comprises a tooth body formed from a model of the subject's tooth), a dental base comprising one or more receiving features (the dental base configured to receive the plurality of teeth models to form a physical dental arch model corresponding to a target configuration of the subject's dental arch), and a dental aligner fabricated using the plurality of physical teeth models attached to the dental base, so that the dental aligner corresponds to the target configuration of the subject's dental arch.

The dental aligners described herein are generally intended to move a subject's teeth from an initial configuration to a final configuration. Thus aligners may be used to straighten teeth or correct malocclusion. These dental aligners may move the subject's teeth by rotating and/or translating the subject's teeth. For example, the dental aligners may rotate at least one of the subject's teeth in one or more directions around its roots when the aligner is worn by the subject. In particular, a dental aligner may rotate at least one of the subject's teeth around its roots in one or more of: the polar direction, the azimuthal direction, and the self-rotation direction. A dental aligner may translate at least one (or more) of the subject's teeth in the x-direction, y-direction, and/or the z-direction.

Another method for treating a subject's teeth includes the steps of: determining a target configuration for the subject's teeth, producing receiving features on a dental base in response to the target configuration (the receiving features being configured to receive physical tooth models), assembling the physical tooth models on the dental base to form a physical arch model, and producing a dental aligner using the physical arch model to move the subject's teeth to the target configuration. The step of producing receiving features on a dental base may include determining the locations of the receiving features on the dental base in response to the target configuration for the subject's teeth, and producing the receiving features at the determined locations on the dental base.

As described above, the step of producing receiving features on a dental base may involve the steps of producing an subject physical arch model by molding a malleable casting material using an impression of the subject's teeth, producing registration features on the subject physical arch model, and separating the subject physical arch model into a plurality of physical tooth models. Each physical tooth model may include one or more registration features.

Determining a target configuration for the subject's teeth may involve the steps of determining an initial configuration of the subject's teeth, determining a final configuration of the subject's teeth, and determining a target configuration for each of a plurality of treatment steps for moving the subject's teeth from the initial configuration to the final configuration. Receiving and/or registration features on a dental base may be fabricated by any appropriate method, including by CNC-based manufacturing, or other computer-controlled methods. In some of the methods, devices, and systems described herein fiduciary marks (e.g., receiving and/or registration features) are fabricated as part of the aligner fabrication procedure.

Also described herein are methods for treating a subject's teeth, comprising determining an initial configuration of the subject's teeth, determining a final configuration of the subject's teeth, designing a movement path from the initial configuration to the final configuration for one or more of the subject's teeth, dividing the movement path into a plurality of treatment steps (each having a target configuration for the subject's teeth), producing receiving features on a dental base in response to the target configuration for the subject's teeth (the receiving features being configured to receive physical tooth models), assembling the physical tooth models on the dental base to form a physical arch model in the target configuration, and producing at least one dental aligner using the physical arch model configured to move the subject's teeth to the target configuration.

The step of producing receiving features on a dental base may include determining the locations of the receiving features on the dental base in response to the target configuration for the subject's teeth and producing the receiving features at the determined locations on the dental base. Further, the step of assembling the physical tooth models on the dental base may include producing physical tooth models from a model of the subject's teeth, wherein the physical tooth models comprise registration features configured to be attached to the receiving features on the dental base.

The physical tooth models may be assembled on the dental base by producing a subject physical arch model by molding a malleable casting material using an impression of the subject's teeth, producing registration features on the subject physical arch model, and separating the subject physical arch model into a plurality of physical tooth models wherein each physical tooth model includes one or more of the registration features. The physical tooth models may be fabricated using CNC based manufacturing, for example, or they may be molded. In general, the dental aligner may be fabricated by vacuum forming the dental aligner using a sheet of aligner-making material over the physical arch model, by molding a malleable casting material over physical arch model in a casting chamber, or by using CNC based manufacturing.

Also described herein are dental treatment systems for moving a subject's teeth. The system may include a storage device configured to store an initial configuration of the subject's teeth, a final configuration of the subject's teeth, a movement path from the initial configuration to the final configuration for one or more of the subject's teeth, and a target configuration intermediate between the initial configuration and the final configuration along the movement path. The system may also include a dental base having receiving features corresponding to the target configuration for the subject's teeth, a physical arch model comprising physical tooth models attached to the receiving features on the dental base, and a dental aligner produced using the physical arch model, configured to move the subject's teeth toward the target configuration. The storage device may be a computer, which may be configured to control the fabrication of receiving features on the dental base at locations in response to the target configuration for the subject's teeth.

Also described herein are dental treatment systems for moving a subject's teeth that include a computer configured to store a target configuration for the subject's teeth, a dental base having receiving features corresponding to the target configuration stored in the computer, one or more physical tooth models configured to attached to the receiving features on the dental base, and a dental aligner produced using the one or more physical tooth models attached to the dental base. Because it is produced from the physical tooth models attached to the dental arch, the aligner is configured to move the subject's teeth toward the target configuration. The computer may be configured to control the fabrication of receiving features on the dental base at locations in response to the target configuration. The computer may also be configured to store an initial configuration of the subject's teeth and a final configuration of the subject's teeth, and a plurality of target configurations corresponding to treatment steps from the initial configuration to the final configuration.

Also described herein are dental treatment systems for moving a subject's teeth. These systems may include a physical arch model comprising one or more physical tooth models each having one or more registration features, a dental base having receiving features configured to receive the registration features of the physical tooth models to form the physical arch model, a computer system configured to store a target configuration for the subject's teeth and to control the fabrication of the receiving features on the dental base, and a dental aligner produced using the physical arch model, configured to move the subject's teeth toward the target configuration.

The computer system may be configured to determine the locations of the receiving features on the dental base in response to the target configuration for the subject's teeth to control the fabrication of the receiving features at the determined locations on the dental base. The computer may also be configured to store an initial configuration of the subject's teeth and a final configuration of the subject's teeth, and to determine target configurations for a plurality of treatment steps from the initial configuration to the final configuration.

Also described herein are dental treatment systems for moving a subject's teeth comprising a computer system configured to store a target configuration for the subject's teeth, one or more physical tooth models comprising registration features, a dental base having receiving features to receive the registration features, a device configured to fabricate the receiving features on the dental base in response to the target configuration under the control of the computer system, and a dental aligner formed over the physical tooth models attached to the dental base, wherein the dental aligner is configured to move the subject's teeth toward the target configuration.

Also described herein are dental treatment methods for moving a subject's teeth having feedback. This method of dental treatment may include the steps of producing a first dental aligner for moving the subject's teeth toward a first target configuration, analyzing the positions of the subject's teeth after the subject has worn the first dental aligner, determining a second target configuration in response to the position of the subject's teeth after the subject has worn the first dental aligner, and producing a second dental aligner for moving the subject's teeth toward the second target configuration. The step of producing a second dental aligner for moving the subject's teeth towards a second target configuration may involve producing a dental base having receiving features (wherein the receiving features correspond to the second target configuration for the subject's teeth, the receiving features configured to receive physical tooth models), assembling the physical tooth models on the dental base to form a physical arch model, and forming a second dental aligner using the physical arch model.

The method may also include the step of creating physical tooth models from the subject's dental arch by producing a template physical arch model using an impression of the subject's teeth, incorporating registration features in the template physical arch model, and separating the template physical arch model into a plurality of physical tooth models wherein each of the physical tooth models includes at least one registration feature. The method may further comprising determining a final target configuration of the subject's teeth, wherein the first dental aligner and the second dental aligners move the subject's teeth towards the final target configuration. Analyzing the position of the subject's teeth after the subject has worn the first dental aligner may involve producing an impression of the subject's teeth after the subject has worn the first dental aligner, and measuring the positions of the subject's teeth using the impression of the subject's teeth.

Also described herein are dental treatment systems for moving a subject's teeth, comprising a first dental aligner configured to move the subject's teeth toward a first target configuration, a measurement device configured to determine the positions of the subject's teeth after the subject has worn the first dental aligner, a dental base having receiving features for receiving physical tooth models, and an analysis device configured to assist a technician in determining a second target configuration based on the positions of the subject's teeth after the subject has worn the first dental aligner (wherein the analysis device is further configured to form the receiving features of the dental base so that they correspond to the second target configuration). The measurement device may be a mechanical location device or an optical scanner. The analysis device may include a computer configured to manipulate a digital model of the subject's teeth, wherein the analysis device comprises constraint logic indicating constraints on movement to of the teeth, as described further herein.

Also described herein are methods of fabricating a dental aligner for a subject, comprising determining an initial configuration of the subject's teeth, determining a target configuration of the subject's teeth from the initial configuration (wherein the teeth in the target configuration are moved from the initial configuration under the constraint of no movement in at least one degree of freedom), and producing a physical model of the dental arch having physical tooth models arranged in the target configuration. The initial configuration may reflect the current configuration of the teeth in the subject's dental arch. The step of determining a target configuration may involve manually determining a target configuration, and may be aided by using an analysis device comprising constraint logic that indicates constraints on the movement of the teeth. The degree of freedom is typically selected from the group of: the x-direction, the y-direction, the z-direction, the polar direction, the azimuthal direction, and the self-rotation direction. The constraint of no movement may mean no translational movement of the teeth in the x-direction, the y-direction, or the z-direction, or no rotations of the teeth around the roots of the tooth in the polar direction, the azimuthal direction, or the self-rotation direction.

Also described herein are dental treatment system for fabricating a dental aligner with movement constraints. This system may include an analysis device configured to allow manipulation of a model of the subject's dental arch from an initial configuration to a target configuration, wherein the analysis device comprises constraint logic indicating constraints on movement of the subject's teeth in the direction of one or more degrees of freedom. The system may also include a plurality of physical tooth models configured to form a subject's dental arch (the physical tooth models having registration features corresponding to the roots of the subject's teeth), and a dental base having receiving features configured to receive the physical tooth models so that the physical tooth models are arranged in the target configuration.

This analysis device may include a computer device configured to decouple the movements of the subject's tooth to rotations around the roots of the subject's tooth and translations of the subject's tooth. As described above, the degree of freedom may be selected from the group of: the x-direction, the y-direction, the z-direction, the polar direction, the azimuthal direction, and the self-rotation direction.

The disclosed devices, methods and systems may provide dental aligner devices. The dental aligner devices so obtained are effective at re-aligning the teeth and may have enhanced comfort when worn. The disclosed devices, systems and methods may significantly reduce the treatment time and cost compared to the prior art systems. Physical tooth models and the dental base can be shared between treatment steps. Physical arch models can be configured and re-configured for different treatment steps. The physical tooth models can be used to form different arch models in different treatment steps, which may significantly reduce treatment costs and cycle time required for each treatment step. A dental base can include a plurality of target configurations each for different treatment steps. The costs of the dental base can be shared between treatment steps. Dental aligners can be conveniently and inexpensively fabricated using the physical arch model.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawings, which are incorporated in and form a part of this specification, illustrate embodiments of the invention and, together with the description, serve to explain the principles of the invention.

DESCRIPTION OF INVENTION

The following detailed description should be read with reference to the drawings. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses, including what is presently believed to be the best mode of carrying out the invention.

It is to be understood that unless otherwise indicated, the methods, systems and devices described herein need not be limited to applications in orthodontic treatments. As one of ordinary skill in the art having the benefit of this disclosure would appreciate, variations may be utilized in various other dental applications, such as fabrication of and/or treatment planning for dental crowns, dental bridges, and aligners. The dental models may also be modified to support research and/or teaching applications. Moreover, it should be understood that variations of the methods, devices and systems described herein may be applied in combination with various dental diagnostic and treatment devices to improve the condition of a subject's teeth.

It must also be noted that, as used in this specification and the appended claims, the singular forms "a," "an" and "the" include plural referents unless the context clearly dictates otherwise. Thus, for example, the term "a tooth" is intended to mean a single tooth or a combination of teeth, "an arch" is intended to mean one or more arches (e.g. both upper and lower dental arches). Furthermore, as used herein, "calculating," and "formulating" may include the process of utilizing manual and/or computer calculations, such as those used to create a numeric representation of an object (e.g., a digital model) or to measure differences in tooth position. For example, a digital representation may comprise a file saved on a computer, wherein the file includes numbers that represent a three-dimensional projection of a tooth arch. In another variation, a digital representation comprises a data set including parameters that can be utilized by a computer program to recreate a digital model of the desired object.

Figure 8:
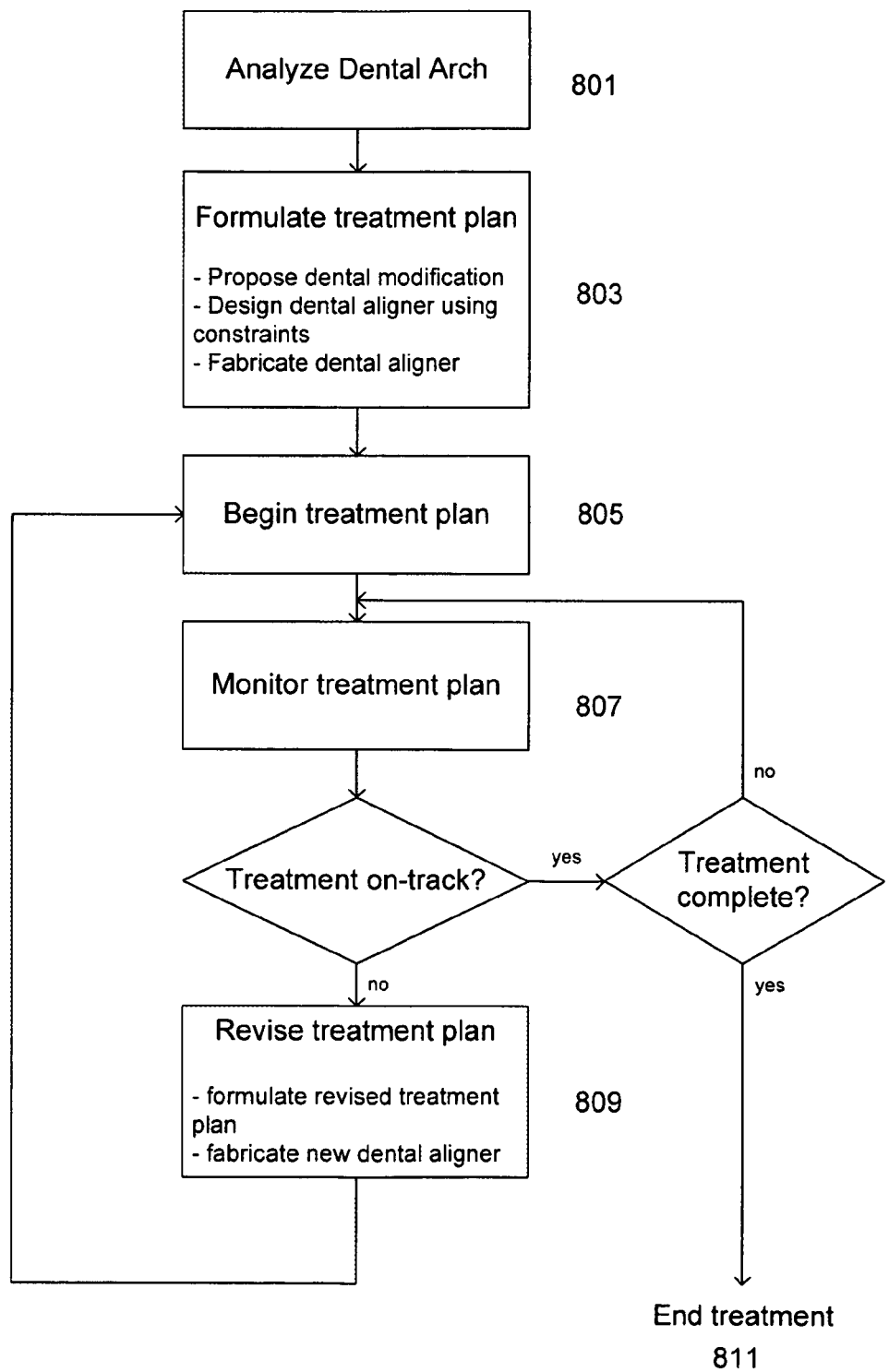
FIG. 8 shows a flow chart describing one variation of a treatment method for treating misaligned teeth as described herein.

Described herein are treatment methods for treating a subject's misaligned teeth. FIG. 8 illustrates a schematic overview of the treatment method. This method generally includes steps of analyzing the subject's dental arches 801, formulating a treatment plan 803, beginning the treatment plan 805, monitoring the treatment plan 807, revising the treatment plan if necessary 809, and continuing the treatment plan until a desired endpoint is achieved 811.

The treatment plan may include any appropriate treatment plan, but typically includes designing and providing a dental appliance (also referred to as a dental aligner) to alter the subject's dental arch. The treatment plan may include steps for analyzing the subject's dental arch, modeling the dental arch, and designing a dental arch to be worn by the subject to alter the dental arch in a desirable manner. The treatment plan may also include steps for preparing the subject's dental arch (e.g., by extracting, shaping, trimming, or otherwise altering one or more of the subject's teeth). Finally, the treatment plan may include steps for designing one or a series of dental aligners, and for fabricating one or a series of dental aligners.

Provided below are examples of treatment methods, including specific steps which may be included as part of a treatment method, or features of the treatment method. In particular, dental aligners that are used as part of a treatment method are described.

Treatment Method

The treatment methods described herein include steps for fabricating of one or more dental aligners. Dental aligners (aligners) may be formed as a series of polymeric dental aligners molded over tooth models. This step typically includes forming sheets of standard, dental grade polymer (e.g., dental grade polymer available from RainTree Essix) over models of the subject's dental arch fabricated from an epoxy cast of the subject's actual teeth, then hand trimming and polishing them to conform to the subject's gingiva.

Separate computerized processes may facilitate the process. For example, a software program may facilitates on-line communication with a dental practitioner, (e.g., orthodontist, doctor, etc.). The subject's dental arch (e.g., dental models) may be scanned to record the tooth positions to help the technician or practitioner manipulate a 3D model of the teeth to graphically depict tooth movement. The recorded tooth positions on the manipulated 3D model may then direct a CNC (Computer Numerical Controlled) machine to drill holes in a base plate into which the individual, epoxy cast teeth are placed for forming. These computer-aided processes expedite the process of mass aligner production the core action of fabricating aligners. A practitioner may progressively adjust the epoxy tooth arrangements to create a new model on which to heat-form aligners. Further description of the computer-assisted steps and method of forming a dental aligner may be found in co-pending PCT application titled "COMPUTER AIDED ORTHODONTIC TREATMENT PLANNING", by Huafeng WEN, Muhammad Ziaullah Khan CHISHTI, Frank Zhenhuan LIU, Kashif MOHAMMED, Syed Wasi Mohsin Raza RIZVI, and Yasser BASHIR, herein incorporated by reference in its entirety.

The practitioner may communicate his or her instructions and adjustments over the course of the treatment process, so that the manufacture of sequential aligners for an individual subject may be modified during the treatment process.

Furthermore, individual subject information (e.g., response to treatment) may be incorporated into the design of the dental aligner, and into the overall treatment method. For example, written instructions and the manipulation of 3D graphics (e.g., digital dental models) may be used to modify the design of dental aligners. This communication may allow a technician to precisely follow instructions or comments from the dental care practitioner (or subject) during each step in aligner fabrication. In contrast, other aligner fabricators techniques do not afford the practitioner the opportunity to adjust aligners (and therefore treatment) on a continuing basis; instead, a computer algorithm determines the tooth movement and the practitioner or subject receives several years worth of dental aligners for treatment at a single time.

The treatment methods described herein provide the practitioner the opportunity to review the treatment (e.g., the current tooth position during treatment) and to modify the treatment by modifying the aligner shape, and effect on the dental arch at appropriate times (e.g., before the next aligner is fabricated).

An exemplary treatment method begins with an analysis of a subject's dental arch. For example, a practitioner (e.g., a doctor, such as a dentist or orthodontist, technician, or the like) may make an impression of the subject's teeth and gingiva. Impressions are typically taken of both the upper and lower jaw. The impressions may be prepared using standard techniques, such as a dental tray filled with polyvinylsiloxane (PVS). In addition to trays with the impressions, a Panorex, bite registration, intra-oral photographs, extra-oral photographs, and a written prescription describing the professional's desired repositioning of the subject's teeth may be used to manufacture a model (or models) of the subject's dental arch, and to help design the subject's treatment plan. As mentioned, a practitioner may submit instructions or observations (e.g., a prescription) describing a desired dental arrangement, or manner of achieving a desired dental arrangement. This prescription may be based upon the professional's observations of the locations of the subject's teeth and possible improvements thereof. This prescription may be transmitted in any appropriate form, including being written on a form that has blanks for identifying which teeth are to be treated, what treatment is desired. The prescription may be freeform or may include a menu of choices. In some variations, the prescription may include specific points such as the inter-proximal reduction (IPR) desired, and may include observations such as which teeth are facially restored (and therefore should not receive anchoring buttons), may include existing occlusion information, may indicate where extractions are to be performed, and/or may indicate other specifics of the treatment to be applied. This information from the practitioner may also be entered into a computerized form by the practitioner in his or her office, and made available on-line via for review by other practitioners or by the aligner manufactures.

This dental impressions, images, and any other data collected from the subject's dental arch may be analyzed in order to model the subject's dental arch. For example, a device called a MicroScribe may be used to identify the location and orientation of each tooth within both the upper and lower impression. Such positional information may then used (e.g., by a CNC machine) to create a "base plate" for modeling the dental arch. The process of modeling the dental arch is described in more detail below, as well as in the references previously incorporated. One variation of this process is summarized here to illustrate a treatment method. A base plate may be used to form a physical model of the dental arch that may also be used to form a dental aligner. For example, the base plate may have holes drilled in locations and orientations corresponding to the positions of the teeth roots. Pins may be placed into these holes, and may act as fiduciary markers, as well as helping to model the movement and position of the teeth. In one variations, pins are approximately 1.6 mm diameter and extend outwardly from the base plate approximately 5 mm.

The subject's dental arch impression (e.g., PVS impression) may then be placed into a casting container along with the above mentioned base plate with the pins inserted. The impression may then be cast (e.g., using a hard epoxy-type material) to form a precision duplicate of a subject's teeth with metal pins embedded inside each tooth. After the epoxy hardens, the castings can be removed from the impressions, forming positive models of the subject's teeth in their initial untreated positions (as well as the subject's gingiva).

In some variations, two model arches, one for the upper arch and one for the lower arch, are made, and put together with the PVS Bite provided. Known points on the 2 arches may be measured to determine the bite relationship between the two arches.

The base plate can then be removed from the positive model. The positive models are cut apart so that each section of the model comprises one individual model tooth and the adjacent gingiva. Typically, each model tooth with its gingiva has two pins protruding from it. As mentioned, these pins may act as both fiduciary markers (showing the relative orientation of the teeth with respect to each other, and may also represent "roots" of the teeth.

Each model tooth can then be individually scanned with a Laser scanner to generate a three-dimensional computer model of the tooth, which includes the exposed surfaces of the model tooth, and the positions and orientations of the two pins that extend from the tooth. A computer model of the arch may be re-constructed based on the scan data. The stored pin positions and the stored virtual model teeth are combined with a random positional generator to create a digital model of the dental arch. For convenience, this digital dental arch is referred to herein as the "working arch."

The positions of the subject's teeth in the virtual (e.g., working) arch(es) may be manipulated into a desired position based upon the input from the practitioner (e.g., the written input provided). A technician may use the digital model to create a target arrangement (typically an intermediate target arrangement) of the dental arch from the working arch. In some variations, the physical march is manipulated to form the target dental arch. The dental arch may be manipulated into a target dental arch by the technician or practitioner. The technician may apply his or her own experience in forming the target arrangement of the dental arch, as well on guidelines set by the practitioner. In some variations, the technician forms the target dental arch based on movement constraints implicit in the movement of the subject's teeth, as described further below. A digital model formed by the target arrangement may also be referred to as a "prescription view" (or "RxView") of the virtual tooth positions, in the virtual arch(es).

The target arrangement of the dental arch may be the final target arrangement, in which the teeth are arranged in a desired final position, or it may be an intermediate target arrangement, in which the teeth are being moved toward the final target arrangement. Each target arrangement (both intermediate and final) may be associated with one or more dental aligners.

Thus, a RxView is typically a visual representation of the technician's interpretation of the prescription from the doctor. Typically, this RxView (digital dental arch model) is not used to fabricate an aligner. For example, this digital dental arch model may have teeth that have small gaps which may not reflect a good treatment, and the teeth may even overlap with each other. The RxView is typically a visual guide that does not direct the physical placement of the epoxy teeth models used, as described below, to generate the aligner.

RxView data may be disseminated to the practitioner. For example, via software running on a web-based account. The practitioner can then either modify the digital dental arch model (RxView) using software, or can send comments suggesting further modification of the target dental arch model. A technician may incorporate these comments.

For example, a technician may manipulate the positions of the subject's teeth in the digital model (either the initial model or the RxView model) using a computer program. The teeth of the dental arch may be manipulated into a position so that an aligner formed to correspond to this position (the "next appliance position") will move the teeth toward the desired alignment. Thus, in the first pass, the dental arch model will be in a "current position" (reflecting the current position of the teeth), and can be moved into the "next appliance" position which is first appliance position. In one variation of this process, the RxView may be used by the technician as a visual reference, but it is typically not a source of digital information used in the manipulations performed by the technician. Rather, the technician's manipulations of the current tooth positions are based upon the technician's visual judgment of how those current positions relate to the desired positions as visually represented in the RxView, and based upon the judgment in the technician's mind of the best approach to moving the teeth from their current positions toward those desired positions.

During this step, the software may impose anatomically-derived limitations (constraints) on the extent of movement and/or force applied to each tooth, e.g., limiting movement to 0.3 mm or less. When tooth movements are completed, the technician typically stores the new virtual arches (having teeth positions corresponding to the positions of the teeth to be achieved by the next appliance). These "next appliance" digital models may include simulated gingiva and roots that may be appended to the exposed surfaces of the teeth that are included in the virtual model teeth.

Prior to manufacture of an aligner using the device, a practitioner may be notified that the "next appliance" model is ready, and can be reviewed. The practitioner may view the virtual arch(es) of the virtual model teeth in their current untreated positions, the virtual arch(es) of the virtual model teeth in the RxView, and the virtual arch(es) of the virtual "next appliance" model teeth as they will be positioned by the forthcoming aligner. The practitioner can modify both the RxView tooth positions, and the positions for the next appliance, using controls by which a tooth may be selected and moved, as described in more detail in some of the patent applications previously incorporated by reference. Typically, the practitioner eventually approves (e.g., via computer access), the (potentially modified) RxView and the (potentially modified) virtual arch tooth positions for the next appliance. The "next appliance" will then be the manufactured. In some variations, multiple (e.g., two) appliances are manufactured at a time. Thus, both an immediately "next appliance" and the appliance following the "next appliance" may be modeled (digitally) and then fabricated as described above.

As described in more detail below, the aligner manufacturing process is used to produce one or more dental aligners using the digital model by forming a physical (non-digital model). Once the RxView is finally approved by the practitioner, the locations of the pins in the virtual model teeth for the first appliance may be used to program a CNC machine, to drill holes (e.g., receiving features) in a staging plate or plates (also referred to as a base plate) that correspond to the positions of the pins of the model teeth for the forthcoming appliance. Model teeth with pins are manually inserted into the holes in the staging plate(s) drilled by the CNC machine, creating a physical arrangement of the teeth in the positions for the appliance to be formed.

An aligner may then be fabricated over the model teeth that are positioned in the staging plate(s), using a "drape and form" process with a dental pressure forming machine, and the aligner can then be trimmed. Aligners may also be fabricated with special features requested by the practitioner, such as buttons and windows to assist certain teeth movement. For example, buttons and windows may be used to help secure the aligner to the dental arch, and may be used to direct force to move the teeth of the dental arch. For example, if such features are requested, small buttons can be installed on the model teeth in the manufacturing process. A template plastics tray will be made to assist the doctors to place the buttons in a subject's teeth. Aligners can then be fabricated with windows (e.g., small cut-outs) at the location of each prescribed button.

After manufacture, the aligners can be marked for case number and subject's name (or otherwise labeled), cleaned, sterilized, and packaged for shipment. In some variations, a box is shipped to the practitioner that includes two plastic bags containing two sets of appliances formed in the preceding steps, plus the templates for buttons, if any. The practitioner examines the appliance (the "next aligner") on the subject to test the fit. During the first visit to the practitioner after impressions have been made, the "next appliance" will be the first appliance. If the practitioner deems the aligner fit to be correct, the subject can leave with the current appliance, and the next appliance, and wears each for three weeks in succession.

During the 6 week period of use of the appliances most recently delivered to the subject, a technician may manipulate the "current" positions of the subject's teeth (which are the positions used to create the appliance(s) most recently delivered to the subject), to move the teeth in the manner the technician believes should be done by the next appliance. This proposed new position may be made available to the practitioner for approval or modification, as described above, and may then be used to form the next appliance, in the manner described above.

The subject typically returns to the practitioner after having worn for each of the two aligners received for the appropriate time (e.g., three weeks). The practitioner may then monitor the effect of the aligner use to determine if the subject is progressing as expected, or if the treatment plan needs to be modified. For example, the practitioner may take additional images of the subject, or may take additional casts of the subject's teeth. The monitoring and analysis of the subject's treatment maybe sent to the manufacturer (e.g., for use by the technician manufacturing the aligners). If no modification is necessary, or after modification, the steps of approval, further modification of the digital model and manufacture of the new aligners is repeated substantially as described above.

These steps may be repeated until the practitioner and/or subject discontinue the treatments. Discontinuing the treatment typically means that the treatment goal has been reached, treatment is terminated, or the practitioner or subject aborts the treatment.

The steps of the treatment methods described herein may include additional step, or may omit steps. Furthermore, any appropriate method may be used to perform the different steps included. For example, any appropriate method or device may be used for designing and forming a dental aligner by modeling the dental arch. In some variations, an aligner is formed by first modeling the dental arch.

Dental Model

A dental model may be created from an actual image, imprint or reproduction of a subject's tooth or teeth, or a model may be produced from measurements or other information derived from a subject or representation of a subject. As used herein, unless the context makes clear otherwise, the terms "model," "dental model," "tooth model," and "arch model" may refer to actual (e.g., physical) or virtual (e.g., digital) models. Further, the models described herein may include all or portions of a single tooth, all or portions of multiple teeth, and all or portions of the dental arches (including the gingival, tooth, root, jaw, etc.). Thus, the models described herein may include information about or representation of any of the features of the dental arches, particularly those features that are relevant to the function and appearance of teeth. For example, the model may represent tooth appearance (e.g., location, size, position, color, shape, orientation, texture, etc.), interaction (e.g., proximity to other dental and mandibular features, kinetics, etc.) and the like.

As used herein, a "subject" may include any subject (human or animal) whose dental structure (e.g., teeth, gingival, etc.) may be modeled by the devices, methods, and systems described herein, including orthodontic patients.

There are many uses for models of a subject's teeth. In particular, the models may be used to understand and to treat a subject's dental alignment. The models may be manipulatable so that different alignments of the subject's teeth may be modeled. In some variations, the models may comprise limitations on the movement or arrangement of teeth (constraints). These constraints may be based on physiological constraints, including the orientation of other teeth, the bite alignment, and the ease or difficulty of moving actual teeth in one or more directions. The manipulatable models may be digital (computer-manipulatable) or physical models.

1. Creation of a Dental Model

A dental model may be created using any appropriate method. Furthermore, the model may be a physical model or a virtual model. For example, models may be constructed from imprints, molds, measurements, images, or measurements of a subject's dental features. One model may be made (or derived) from another model. Thus, a physical model may be made from a virtual model, and a virtual model may be made from a physical model. In particular, a model may be altered and then one or more derived models may be generated from the original model. For example, components of a model (e.g., individual teeth) may be moved slightly to form a second model. Thus, the model may represent the actual arrangement of a subject's teeth, or a derived arrangement. Features not present on a subject's teeth (e.g., crowns, dentures, etc.) may be included as part of the dental model.

In one variation, a model may be generated using a mold (e.g., a positive or negative model) of a subject's upper dental arch and a mold of a subject's lower dental arch. In addition, a registration device (e.g., a bite-down registration device) may also be used to model the subject's bite registration. Fiduciary references may be used to align any of the components of the model.

For example, at the start of the modeling procedure, a physical model (e.g., mold or cast) may be made of a subject's upper and lower dental arches. Any appropriate method of making a cast or model of a subject's dental arches may be used. In one variation, a negative mold is made from all (or a portion) of a subject's upper and lower arches. For example, a dental cast made be made showing the arrangement of the subjects upper and lower teeth with respect to each other. A positive replica may then be formed using this negative mold. The positive and negative mold may also be used to accurately model the relationship of the individual teeth with respect to each other, as described in many of the patent applications mentioned above. Other examples of molding dental arch models are disclosed in the above referenced U.S. patent application Ser. No. 11/013, 160 ("System and methods for casting physical tooth model"), and U.S. patent application Ser. No. 10/979,823 ("Method and apparatus for manufacturing and constructing a physical dental arch model").

Thus, a dental model may be made for the subject's current arrangement of teeth (or "initial" arrangement). The dental models may include any feature of the actual dental arches, or a subset of these features. For example, the dental model may include the crown regions of the teeth, the gums (gingival), the roots, etc. Some of these features may be actually measured or derived. For example, the structure and locations of the roots of the teeth may be calculated (or computer-generated) from measurements taken from the crown region or other portions of a subject's teeth or mouth, as described in U.S. Provisional patent application titled "COMPUTER AIDED ORTHODONTIC TREATMENT PLANNING" by Huafeng Wen, et al, filed Apr. 19, 2005.

In some variations, the dental model may be made by directly scanning a subject's teeth. For example, an intraoral 3-D imaging device, such as OraScanner® manufactured by OraMetrix®, can be utilized to digitize the subject's tooth arch. The digital dental arch model is subsequently segmented into individual teeth, which comprises digital representations of the crown portion of the individual teeth. In one application, the scanning of the subject's teeth is conducted at the dentist's office. The data generated from scanning, i.e., the digital representation of the subject's arch, is then transmitted over a computer network to a receiving computer for further processing.

A physical dental model may also be used to construct a digital dental model. For example, a positive model of the subject's tooth arch may be created from a negative impression of the subject's teeth. The teeth of the positive mold may then be segmented into individual units (e.g., teeth) and digitized or scanned by various 3D scanning techniques and reconstructed to digitally represent the subject's upper or lower arch. Examples of appropriate scanning techniques that may be used to create a digital model are described further below. A physical model of the dental arches may also be made from a digital model. For example, physical models of the upper and/or lower arches may be fabricated using Computer Numerical Control (CNC) manufacturing (such as milling, stereo lithography, and laser machining).

It may also be beneficial to include markings such as fiduciary references on the upper and lower arch models.

2. Fiduciary References

Fiduciary references may be used to aligning the teeth to form the dental model. Virtually any mark, object or region of an object may be identified as a fiduciary reference for purposes of aligning the arch models. A fiduciary reference may be a stereotyped reference mark by which the orientation and/or location of an arch model or components of an arch model (e.g., individual teeth) may be identified. A fiduciary reference may include multiple marks, or an asymmetric mark. Fore example, a fiduciary reference may be a point or set of points scribed onto the arch model or onto an object to which the arch model is attached.

In some variations, a model includes a fixture that may be a plate (e.g., a base plate or dental plate) that is not part of the subject's actual dental arch, but to which the dental arch model is attached. The fixture may comprise a fiduciary reference. Components of the dental arch (e.g., individual teeth models) may be secured to the fixture so that the dental arch does not change position relative to the fixture. Thus, the fiduciary reference(s) may be marked on the dental arch itself or it may be marked on the fixture, or both. In one variation, the fixture comprises attachment or receiving sites that mate with fiduciary components on the teeth models to provide fiduciary reference. Thus, the fixture may include engagement surfaces to align (and/or secure) other components of the dental model.

For example, the tooth models may comprise registration features compatible with the receiving features on the dental plate. Examples of registration features that may be used include, but are not limited to pins, protrusions, posts, snaps, and the like. In some variations, the registration features may model the orientation of the roots of the teeth. In registration systems as described above, the individual tooth models may be used with different dental plates in order to show different arrangements of the teeth. For example, if a tooth is to be moved to create a modified dental model, the model may be readily constructed by moving the receiving feature on the dental plate, and using the same tooth model. Additional examples of registration features are described in the Examples given below.

The location and orientation of the fiduciary marker may be selected by the user ("user" may refer to the technician, manufacturer or in some cases, practitioner), or may be automatically selected (e.g., as by a computer). For example, the user may indicate on a scan of the dental arch where to place registration features (e.g., pins) on each tooth.

Fiduciary references may include any number of markers. For example, a single fiduciary mark may be used to indicate location and orientation of dental arch components. A fiduciary reference may comprise two, three, or more individual marks. In some variations, the fiduciary reference is a three-dimensional structure (e.g., a cut, a pit, etc.). In some variations, the fiduciary reference is a two-dimensional structure (e.g., a mark). In some variations, the fiduciary reference may comprise a color or texture that is distinguishable from the rest of the dental arch model.

As described, a registration device may be used to more accurately model a subject's dental arches. For example, a bite-down registration device may be used, and may comprise a material that conforms to the spaces between the upper and lower arches when the subject bites down (e.g., a wax bite). Additional materials may be used to form the dental models, including images (scans, X-rays, etc.) and the like.

Scanning

The teeth (e.g., a model of the teeth) may be scanned or measured to determine the position of the teeth. Any appropriate technique may be used to measure the positions of the teeth, including manual measurement, contact scanning and non-contact types of scanning Contact scanning includes scanning by actual (or computer assisted) measurement, including mechanical location devices such as a Microscibe. The scanner may be used to acquiring coordinates (e.g., 3D coordinates) from the dental arches including the fiduciary references.

For example, a Microscibe is a 3D digitizer that can develop a digital computer model from an existing 3D object. Exemplary Microscribes are available from Immersion and Phantom. A contact Microscibe scanner may comprise one or more mechanical arms that have mechanical joints with precision bearings including sensors. For example, the Microscibe may move a stylus over the dental model and record accurate 3D positional and angular information of the points that the stylus touches. Thus, the stylus may touch (or be directed to touch) the teeth, base plate, and any fiduciary references. The mechanical location device may also comprise additional sensors (e.g., a sensor located on the tip of the stylus of a Microscribe) for specifically or automatically detecting the fiduciary reference. Examples of additional sensors include optical sensors, RF sensors, and the like.

When scanning a physical dental model, the model may be broken into pieces (e.g., by tooth) for scanning of the individual pieces. The individual scans may then be re-assembled later (using the fiduciary marks, for example). Furthermore, it may be advantageous to set or affix the model (or model pieces) to a scan plate (e.g., a surface from which the scanning may take place). For example, the model may be attached to a scan plate that rotates or otherwise moves to position the assembly so that it might be accurately scanned. In some variations, the assembly is secured to a scan plate.

The dental model (or teeth) may also be scanned by non-contact methods. Examples of 3D non-contact scanners and scanning techniques include, but are not limited to, laser scanning, optical scanning, destructive scanning, CT scanning, and sound wave scanning. In some variations, images (e.g., X-rays, etc.) may be analyzed to determine the position of dental components. This analysis may include image analysis techniques, such as tomography.

The scanner may communicate with a computer that may be used to control the scanning, and/or to store information from the scan. Position and orientation information can be obtained, stored and analyzed. The computer may also act as a controller, and may control other portions of the scanning process, including the scan plate. For example, the computer may allow user input, and may also provide output.

For each portion of the dental model, a fiduciary reference may also be scanned as part of the individual scans, and digital models of the teeth (dental arches) are made from these scans. Each digital model may have its own coordinate system. In some variations, an individual arch may be scanned in pieces or sections, and later reconstructed to form a model of a single dental arch, having a single coordinate system.

Based on the positional information identified from the scanning, the relative positions of the teeth may be calculated, and movement of the teeth after or between treatment steps may be measured.

Aligners

The term "dental aligner" may refer to a dental device for rendering corrective teeth movement or for correcting misaligned teeth. One or more dental aligners can be worn on the subject's teeth so that a subject wearing the dental aligners will gradually have his or her teeth repositioned by the dental aligner "pushing" (or pulling) against the teeth, or gums (gingiva).

Aligners may be fabricated from the dental models described herein. Details of fabricating dental aligners are disclosed in the above referenced U.S. patent application Ser. No. 10/979,497, titled "Method and apparatus for manufacturing and constructing a dental aligner" by Huafeng Wen, filed Nov. 2, 2004, U.S. patent application Ser. No. 11/074,301, titled "Dental aligner for providing accurate dental treatment" by Liu et al, filed Mar. 7, 2005, U.S. patent application Ser. No. 11/074,297, titled "Producing wrinkled dental aligner for dental treatment" by Liu et al, filed Mar. 7, 2005, U.S. patent application Ser. No. 11/074,300, titled "Fluid permeable dental aligner" by Huafeng Wen, filed Mar. 7, 2005, and U.S. patent application Ser. No. 11/074,298, titled "Disposable dental aligner by Huafeng Wen, filed Mar. 7, 2005.

Any appropriate fabrication method may be used to form a dental aligner from the dental model. For example, a dental aligner can be made by molding a malleable casting material in a casting chamber. The mold can include at least a portion of a dental arch model. The dental arch model can include a plurality of the subject's physical tooth models that are positioned in the target configuration specified for the specific treatment step.

The dental aligners can also be fabricated by a Computer Numeric Control (CNC) based manufacturing. A CNC based drilling or milling machine can receive a digital aligner model as input and produce a dental aligner compatible with the target configuration at the specific treatment step. Details of producing physical dental arch model and associated base are disclosed in the above referenced and commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

In one variation, the dental aligner is formed from a dental model by vacuum forming. For example, a sheet of aligner-making material is attached to a sheet holder and then lifted up near a heating element. The sheet can be made of uniform distribution of a single material or comprise multiple layers of different materials. After the aligner-making material is heated by a specified time, the sheet holder is pressed on the subject's dental arch model on the base plate. A vacuum pump removes air at the bottom of the base plate to cause the softened aligner making material to relax and fittingly form around the surface the subject's dental arch model. This process of aligner making is referred to as the vacuum forming.

In one embodiment, the subject's dental arch model includes through holes which may mate with connectors attached to the subject's teeth. Examples of such snap-on aligner are described in U.S. Provisional Application, titled, "DENTAL ALIGNER DEVICES HAVING SNAP-ON CONNECTORS," by Huafeng Wen, et al. filed Apr. 15, 2005, herein incorporated by reference in its entirety.

One or a plurality of dental aligner can be provided to the subject at each step of the dental treatment. Each of the aligners can be worn for a period of time from a few hours to a few weeks. The teeth movement caused by the dental aligner is normally not exactly the same as designed by the treatment plan.

In general, aligners are fabricated so that they apply force to move the teeth, resulting in the re-alignment of the teeth. Thus, aligners are typically fabricated using models that represent the teeth in positions which have been shifted slightly in a direction leading to a desired alignment position, so that the teeth will tend to move towards the desired position. The selection of the ultimate (e.g., desired) position of the teeth, as well as the movement path to move the teeth into the desired position may be chosen by an orthodontist.

Selecting the Movement Path

A dental model may be used to determine a final position for aligning teeth. For example, an orthodontist may manipulate a dental model to determine the final alignment position of the teeth. In some variations, the orthodontist may use computer software to determine the final position of the teeth. The final position of the teeth may be used to determine a movement path in order to move a subject's teeth from a first position (e.g., the initial position or a subsequent position after staring the alignment process) to the final position.

The movement path may be selected manually, automatically, or it may be selected by a user with computer assistance. Examples of methods, devices and systems for choosing a final position and/or a movement path for aligning a subjects teeth may be found in many of the patent applications previously referred to and incorporated by reference, including U.S. patent application Ser. No. 11/013,145, titled "Fabricating a base compatible with physical dental tooth models" by Huafeng Wen, filed Dec. 14, 2004, U.S. patent application Ser. No. 11/013,156, titled "Producing non-interfering tooth models on a base" by Huafeng Wen, filed Dec. 14, 2004.

For example, software may be used to assist the user in choosing a final alignment of a subject's teeth. In one example, digital representations for the teeth are provided from a digital tooth arch model. A digital tooth arch model is then utilized to provide visual feedback to the user when the position and/or orientation of one or more of the individual teeth within the tooth arch are modified. Individual physical models of the teeth within a subject's tooth arch may be used to represent the tooth arch.

In another variation, software running on a computer generates a user interface to allow the user to display and modify one or more of the teeth within the tooth arch model. The position of individual teeth within the tooth arch model may be electively modified (e.g., displaced, rotated, etc.) relative to the other teeth in the tooth arch model. The user interface may display the pre-modified tooth arch model and the post-modified tooth arch model in a side-by-side manner. This display permits the user to verify the changes by comparing the modified arch with the original arch (starting arch). Three or more digital arches models of the same subject may be provided with various changes or adjustments to one or more of the teeth. The user interface may be configured to allow the user to select any two of the arch models and display them side-by-side for comparison.

In some variations, once a target (or final) alignment positions for the teeth has been determined, the movement pathway may be determined. The movement pathway may be calculated based on a number of parameters, including the total distance of tooth movement, the difficulty in moving the teeth (e.g. based on the surrounding structures, the types and locations of teeth being moved, etc) and other subject-specific data that may be provided. Based on this sort of information, the software may generate an appropriate number of intermediary steps (corresponding to a number of treatment steps, or aligners to be manufactured). In some variations, the user may specify a number of steps/aligners, and the software maps different aligner configurations accordingly. Alternatively, the movement pathway may be guided by (or set by) the user.

In one example, a series of nine pairs of different tooth arches, representing projected teeth positions during the course of an orthodontic treatment plan, are generated by a computer after the user selects the final alignment position. The user may elect any of the tooth arches within the treatment plan and display them in a side-by-side manner. The user may be permitted to make changes to the teeth within the tooth arches. For example, one window may show the tooth arch with the teeth in the original untreated positions. A second window may show the tooth arch with the teeth in their indented target positions. The user may modify the tooth arches in a window if desired. An aligner may then be created based on the modified tooth arch in the window based on the digital representations of the tooth arches at different stages of the treatment.

Software may also be configured to allow the user to rotate the tooth arch, such that the tooth arch can be examined from different views. In one variation, the two set of arches in right and left windows are always shown in the same directional view, such that if the user rotates the post-modified tooth arches in the right window, the corresponding pre-modified tooth arches will also rotate in the same direction and in the same amount. If the pre-modified tooth arches in the left window is rotated by the user, the corresponding post-modified tooth arches will also rotate in the same amount simultaneously. In one variation, a curser controlled by a computer controller (e.g., a computer mouse, touch pad, etc.) may be utilized to drag the digital representation of the tooth arch shown in the user interface to rotate the tooth arch. Optionally, icons representing selective predefined views of the tooth arch may be provided within the user interface, such that the user can show a desired view by selecting an icon. In one variation, by clicking on an icon, the tooth arches displayed in different windows will be changed to show selected view of the tooth arches.

The computer software may simulate constraints to movement when both selecting a final tooth conformation and when choosing a movement pathway. For example, the digital representation of the teeth may simulate potential collision between the teeth as the positions of the teeth are modified by the user or through a computer program. In addition, boundary conditions may be predefined to limit the amount of movement of the tooth (e.g., root rotation). For example, rotation of the crown of a tooth may cause large displacement at the tip of the root, which can cause the root to collide with the root of an adjacent tooth. In one variation, the computer software is configured to detect collision when a boundary parameter representing a first root is crossing over a boundary parameter representing a second root. The software may indicate to the user that collision has occurred, or may simply not allow a movement pathway in which collision will occur. In another variation, once collision has been detected, the software will not allow the user to rotate the tooth further in the collision direction, and may begin looking for a different movement pathway to achieve the same (or a similar) final alignment position. In another example, each of the teeth (i.e., crown and/or root) is represented by a mesh of points. When the mesh of points representing the first teeth and the mesh of points representing the second teeth occupies the same space, this would indicate that the two teeth have collided.

In another variation, boundary parameters may be defined to simulate physiological conditions in the subject's mouth and jaw that would limit the rotation and/or displacement of the tooth. In one example, the software utilizes boundary parameters to prevent over-rotation of the teeth. For example, a boundary condition may be defined for each tooth to limit the amount of the rotation and/or displacement that can be prescribed by the user. The boundary condition may be generated based on population sample data of humans' teeth, gum, and jaw structures. The boundary condition may then be utilized to prevent the user from directing the rotation or displacement of the teeth to an unrealistic condition. Furthermore, boundary conditions may be determined for different population subgroups. For each subject, the boundary condition from the appropriate population sub-group that matches the subject's physical parameters may be used to provide better estimation of the physiological limitations. In some variations, the boundary conditions may be determined for each individual patent based on data supplied (e.g., from X-rays, the model, etc).

The practitioner (e.g., an orthodontist) may manually determine (e.g., by entering into the computer) a movement pathway, or the computer may generate a suggested movement pathway. In either case, the user may adjust the movement pathway either before making any aligners, or after the subject has begun wearing an aligner or series of aligners. This allows the orthodontist to correct the prescription if necessary. Furthermore, the user may provide comments or instructions that may be used when creating the movement pathway and/or the corresponding aligners. Thus, the orthodontist may modify his prescription for a new aligner by modifying one or more of the teeth in the digital representation of the tooth arch.

1. Constraints on Movement

As described above, movement of components of the model (e.g., the teeth) to formulate a movement pathway or a final alignment may be constrained by various factors.

Figure 3A:
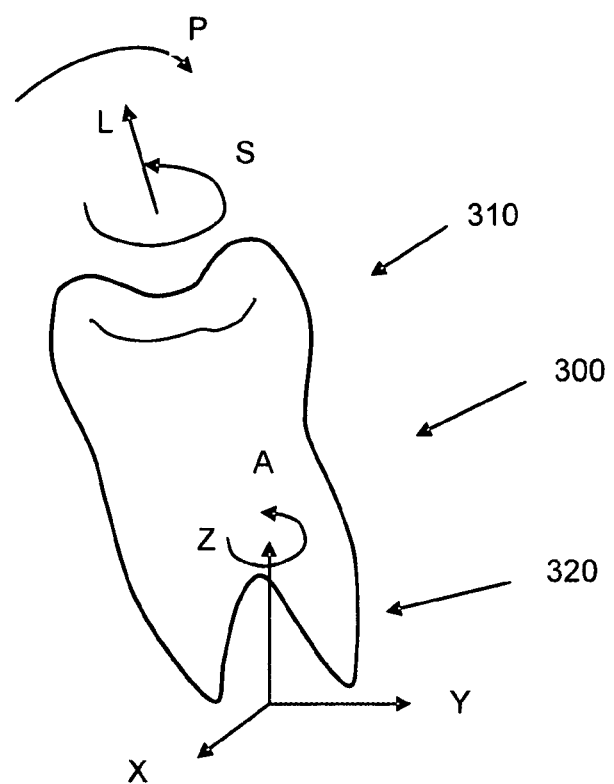
FIG. 3A illustrates a subject's tooth and decoupling of movements.
Figure 3B:
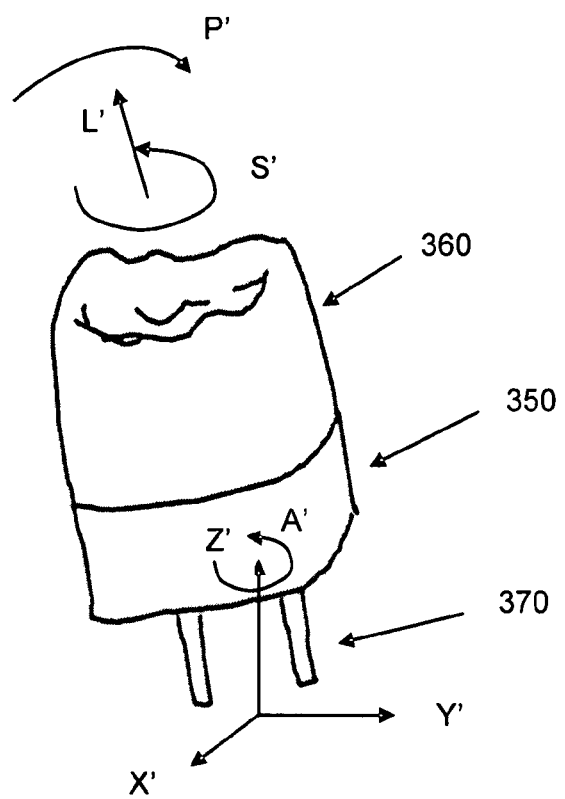
FIG. 3B illustrates a tooth model that can simulate the movements of the subject's tooth in FIG. 3A.

A tooth model may be described as having a tooth body and tooth roots. In general, the tooth movements can be decoupled into rotations around the roots and translations of the roots. The translations of the roots may be described by a coordinate system, such as a Cartesian coordinates defined by X-, Y-, and Z-axes. In one variation, movement of the tooth roots may be though of as movement of the center of the tooth separate from the "orientation" of the tooth. The longitudinal axis, L, of a tooth can rotate along a polar direction P, a direction of self-rotation S, and an azimuthal direction A. Movement in P, S and A may be thought of as orientation movements. Although alternative descriptions of movements exist, his definition of the tooth movement has the advantage of decoupling the large (rotational) orientation movements from small (translational) movements. Since the roots are generally anchored, the easiest movements of a tooth 300 under external forces are the rotations around the roots, whereas the translations of the roots are of much smaller magnitudes. Thus, the rotation or orientation movements can be viewed as movements about a pivot point about which the tooth rotates. FIGS. 3A and 3B illustrate these axes of movement (X,Y,Z) and (P,S,A).

Thus, movements of the tooth model can be described by coordinate systems identical to those used for the subject's tooth. For example, the roots of the teeth may be simulated by the registration features, as described above. Translation of the registration features may be described by a Cartesian coordinate system based on the X'-, Y'-, and Z'-axes, and rotation of the tooth model can be described by the rotations of the longitudinal axis L' of the tooth model along the polar direction P', the self-rotation direction S', and the azimuthal direction A'.

In some variations, movement in one or more of these directions is limited or constrained. For example, when planning the movement pathway (or helping the user select a movement pathway) the software or physical model may prevent certain types of movement (e.g., in constrained direction) or may prefer alternative types of movement in order to achieve a final alignment of the teeth. In some variations, the software may "weight" certain types of movement differently, e.g., corresponding to the difficulty in moving in one or more directions. These weights may be used in calculating the movement pathways. In some variations, the software may tell the user when a movement in a constrained direction has been chosen, or the software may simply prevent the technician or practitioner from selecting movement in that direction.

In some variations, because the registration features mimic the roots of the subject's teeth, the tooth models attached to the dental base can most closely simulate the present or the target configurations of the subject's teeth. The movements of the subject's teeth are decoupled to large movements (i.e. rotations around the registration features or the roots of the teeth) and small movements (i.e. translations of the registration features or the roots). The dental aligner can therefore be designed to focus on the large movements at each treatment step, which normally involves minimal translation of the roots. Dental aligner can be thus be formed using the tooth models generated at various points along the movement pathway. Thus, a treatment series may be generated having some number of positions (e.g., an initial or starting position, a first treatment position, a second treatment position, etc. until achieving a final position).

In some variations, the practitioner may adjust the treatment positions while the subject is still undergoing treatment, either based on user preference or based on feedback from the subject's treatment to date.

2. Feedback in Forming the Movement Pathway

As described above, a movement pathway may be adjusted during treatment of a subject. For example, after selection of an alignment pathway, and construction of one or more aligners, additional subject data (e.g., teeth measurements taken during treatment) may be used to refine or alter the movement pathway and therefore re-design the movement pathway, possibly including the final alignment position. In some variations, the practitioner (e.g., an orthodontist) may refine the treatment pathway, including the final position, during treatment.

In some variations, the treatment path may be modified by measuring the actual position of the subject's teeth during the alignment procedure. For example, measurements of the subject's teeth may be taken by any appropriate method, including the scanning methods previously described. In one version, a negative impression of the subject's teeth is taken at some point during the treatment period, after the subject has worn an aligner. Measurements taken from the subject's teeth may then be compared to the initial position, the final position, and any of the intermediate treatment positions. These measurements may then provide information that is feed back into the design of the next treatment steps.

In some variations, measurements taken during treatment may provide subject-specific information on how responsive a subject is to the treatment, and may allow further customizing of the treatment. For example, if a subject has worn a first aligner (corresponding to a first alignment position) for a specified amount of time, the movement of the teeth from the original position to the first alignment position may be determined by comparing the actual position of the teeth after wearing the first aligner to the initial and first alignment positions. The movement path may then be modified to correct for differences between the anticipated first alignment position and the actual first alignment position. In some cases, additional alignment steps may be added to the movement pathway, or the movement pathway may be changed to indicate previously unsuspected constraints on the movement of some or all of the teeth.

Described below are Examples of many of the different components of the devices, methods and systems of alignment described herein. Any of the steps described may be used in combination with any of the other steps, or parts of other steps.

EXAMPLES

Example 1: Treatment Method with Feedback

Figure 1A:
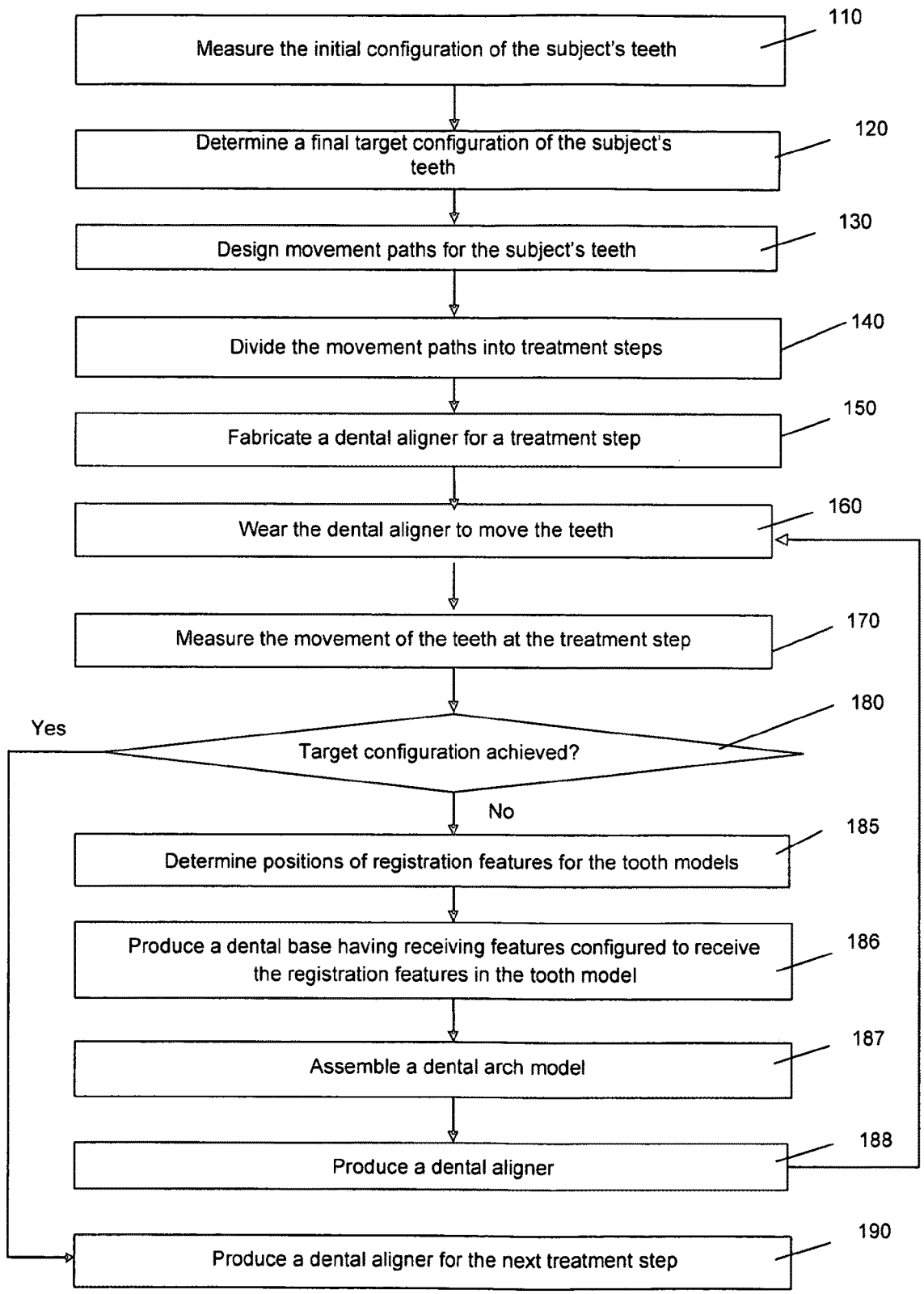
FIG. 1A is a flow chart for providing accurate orthodontic treatment for a subject in accordance with the present invention.

FIG. 1A illustrates one method for providing orthodontic treatment for a subject using feedback. First, the initial configuration of the subject's dental arch(s) is measured 110. The initial configurations of the subject's teeth can include the positions and the orientations of the subject's teeth before the treatment begins. The analysis of the initial configuration of the subject's teeth can include making dental impressions of the subject's upper and/or lower arches. A digital model of the subject's dental arches can then be produced. The surface locations of the dental impressions can be measured to determine the positions and the orientations of the subject's teeth, as described above and in the incorporated references. For example, details of conducting measurement on dental impressions are disclosed in the above referenced U.S. patent application Ser. No. 11/013,159, titled "Producing a base for accurately receiving dental tooth models" by Huafeng Wen, filed Dec. 14, 2004 and U.S. patent application Ser. No. 11/013,157, titled "Producing accurate base for dental arch model" by Huafeng Wen, filed Dec. 14, 2004.

A practitioner may determine a target configuration for the subject's teeth. This target configuration may be a final target configuration 120 (e.g., indicating a final configuration of the teeth at the end of the treatment), or it may indicate an intermediate target configuration. The practitioner may indicate a target configuration by manipulating a physical or digital model and providing the manipulated model, or by providing verbal or written instructions on how the teeth should be positioned with respect to their current position (or other reference), or some combination thereof.

The practitioner may design a treatment plan by determining a target arrangement of the teeth 120 (e.g., a final target arrangement). As mentioned above, a final target arrangement does not have to be explicitly determined at the early stage; treatment can begin and the practitioner can settle on the final arrangement only after seeing how the subject's teeth respond to treatment. Once a target arrangement is determined, a movement path may be determined 130. The movement path is the path taken by the teeth as they are moved by the aligner or aligners in order to achieve the target arrangement. The aligners typically move the teeth incrementally. If the movement path requires that the teeth move more than a predetermined amount (e.g., 0.3 mm or less in X or Y translation), then the movement path may be divided up into multiple steps, where each step corresponds to a separate target arrangement 140. The predetermined amount is generally the amount that an aligner can move a tooth in a particular direction in the time required for each treatment step (e.g., 3 weeks). A dental aligner may be fabricated for each of these treatment steps 150.

The movement path may be determined with the assistance of an analysis device such as a computer analysis device (e.g., a computer running analysis logic). For example, the analysis device may be configured to include constraint logic that indicates the constraints on the movement of the teeth, as described above. Thus, the movement path may be explicitly indicated by the practitioner, or may be suggested by the analysis device and approved by the practitioner. In some variations, the movement pathway is generated by a technician with the assistance of analysis software (see Example 2, below). The computer analysis device is typically configured to store the initial and the target configurations (e.g., final and intermediate target configurations) of the subject's teeth as well as the movement path(s) from the initial configuration to the target configuration. The movement path may avoid teeth collision and overlap, and may also take into account movement constraints for the teeth, including constraints on how much a tooth may move during a given treatment step.

As mentioned, the movement paths may be divided into a plurality of successive treatment steps 140. There can be, for example, ten to forty steps. One or more dental aligners can be fabricated for each treatment step 150. The subject wears one of the dental aligners to move his or her teeth as part of each step 160.

Dental aligners may be fabricated as described herein. One or a plurality of dental aligner can be provided to the subject at each step of the dental treatment. Each of the aligners can be worn for a period of time from a few hours, to a few weeks (e.g., 3 weeks). Aligners may be worn continuously over for a portion of a day.

As described, orthodontic treatment methods may include "feedback" allowing the teeth to be iteratively adjusted during treatment based on how the teeth have responded to one or more of the dental aligners. Thus, one or more aligners may be designed for future treatment steps only after analyzing the arrangement of the subject's dental arch after the subject has worn a dental aligner as part of the ongoing treatment.

The teeth movement caused by the dental aligner is normally not exactly the same as designed by the treatment plan. Thus, as described above, the movement of the teeth may be analyzed after an aligner has been worn 170 to determine their position, in the dental arch, or how much they have moved since beginning the previous treatment step (or steps). The movement resulting may be factored into the treatment plan, particularly in the design of additional aligners. The positions and orientations of the subject's teeth can be measured, which can serve as a feedback to the adjustment of the treatment plan.

Figure 2:
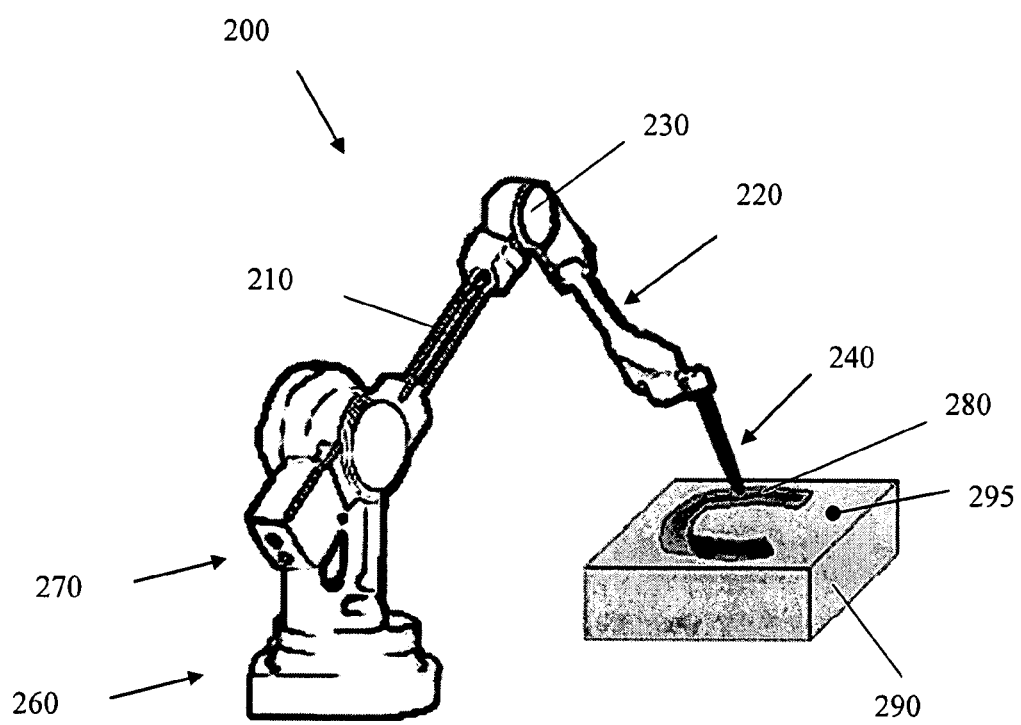
FIG. 2 illustrates an exemplified mechanical location device for acquiring the surface locations of dental impression and subject's teeth positions.

A negative impression of the subject's dental arch can be obtained after the subject has worn the dental aligner for a period of time, and measurements taken as described above for determining analyzing the configuration of the subject's dental arch. FIG. 2 illustrates one method for determining the configuration of a subject's dental arch. A subject's negative dental impression 280 can be fixed in a container 290 using an epoxy. The container 290 can be marked by one ore more reference marks 295 that can define the coordinates of the impression 280. The relative positions of the subject's teeth are measured off the impression using a mechanical location device 200. An example of a mechanical location device is the Microscribe available from Immersion and Phantom. Microscribe is a hand-held 3D digitizer that can develop a digital computer model for an existing 3D object. The mechanical location device 200 can include mechanical arms 210, 220 having one or more mechanical joints 230. The mechanical joint 230 is equipped with precision bearings for smooth manipulation and internal digital optical sensors for decoding the motion and rotation of the mechanical arms 210, 220. The end segment is a stylus 240 that can be manipulated to touch points on the dental impression 280 held in the container 290. The mechanical location device 200 can be fixed to a common platform as the container 290. Accurate 3D positional and angular information of the points that the stylus touches can be decoded and output at the electronic output port 270. The positional and orientational information can be obtained by additional decoders. Additional sensors can be placed at the tip of the stylus to measure the hardness of the surface of the measurement object. Immersion Corp.'s MicroScribe uses a pointed stylus attached to a CMM-type device to produce an accuracy of 0.009 inches.

In measuring the teeth positions from the impression of the subject's teeth, the MicroScribe digitizer is mounted on a fixture fixed to a base plate. The device can communicate with a host computer via USB or serial port. A user (e.g., a technician or manufacturer) then selects points of interest at each tooth positions in the impression and places the stylus at the point of interest. Positional and angular information are decoded and then transmitted to the computer. The Cartesian XYZ coordinates of the acquired points are then calculated and logged for each first feature location and orientation (or alternatively each tooth).

A new coordinate system is established based on the container chamber in which the arch impression is held. This system is established by taking readings for two points on two sides of the container to define the x-axis. Another reading on the plane establishes the x-y plane. An origin is then determined on the x-y plane. The z-axis will be established by taking the cross product of the x-axis and y-axis.

The user next selects a plurality of points on the surfaces of the arch impression corresponding to each tooth. The 3D points measured from the impression surfaces are then interpolated to create surfaces and solids integrated into an overall design.

The number of points defining the curves and number of curves depends on the desired resolution in the model. Surfacing functions offered by the design application are used to create and blend the model surfaces. The model may be shaded or rendered, defined as a solid or animated depending on the designer's intentions. All the readings acquired by the stylus can be rendered in real time to allow the user to visualize the digital tooth models. The coordinate axes and points can be rendered in the software using different colored cylinders/spheres etc. so as to distinguish the different meanings of values.

The teeth positions can also be obtained by optically scanning the dental impression or tooth models molded using the dental impression. An optical scanning system can include a scan table on which the dental impression or the tooth models can be mounted. The scan table can be rotated by a rotation mechanism under the control of a computer. One or more image capture device can capture images of the dental impression or tooth models molded as the scan table is turned to an angular position. The optical axis of the image capture device can be for example 45 degree off the vertical axis (or the top surface of the scan table).

A digital dental arch model can include a plurality of digital tooth models. The digital dental model can be developed based on the first feature locations and orientations or alternatively the coordinates of the physical tooth models acquired by the mechanical location device.

The images of the dental impression or tooth models are analyzed. The coordinates of a plurality of surface points on the dental impression or tooth models are computed by triangulation using the captured image data. The surfaces of the dental impression or tooth models are constructed by interpolating computed coordinates of the points on the surface. The positions of the subject's teeth can thus be obtained. The positions of the subject's teeth can also be measured by a laser tracking system and a motion tracking system. Details of measuring location information on a dental impression of a subject are disclosed in the above referenced U.S. patent application Ser. No. 11/013,159, titled "Producing a base for accurately receiving dental tooth models" by Huafeng Wen, filed Dec. 14, 2004 and commonly assigned U.S. patent application Ser. No. 11/013,157, titled "Producing accurate base for dental arch model" by Huafeng Wen, filed Dec. 14, 2004.

The measured positions of the subject's teeth are compared to the target configurations at the treatment step in the treatment plan in step 180. If the target configurations are achieved within a specified tolerance, the treatment can proceed according to the original design. One or more aligners can be produced for the next treatment step as originally planned in step 190.

If it is found that the dental aligner did not move the subject's teeth to the desired target configurations in step 180, the orthodontist can design another dental aligner in response to the measured current teeth positions and the desired positions for the subject's teeth at this stage of the treatment. Typically, the orthodontist uses computer software to simulate the teeth movement to the target configurations for the subject's teeth. The target configurations include desired teeth positions and orientations. The target configurations can be specified in the original treatment plan for this or the next step of the treatment. Furthermore, the orthodontist can also dynamically adjust the target teeth configurations for the next treatment step in accordance to the movement of the subject's teeth.

As described, dental aligners can be fabricated with the assistance of physical tooth models that can be assembled to form a physical dental arch model. The physical dental arch model can be formed on a dental base. The physical tooth models of the subject's teeth can be fabricated and used for one or more treatment steps. The dental base can include a plurality of receiving features for receiving the tooth models. The tooth models can comprise registration features compatible with the receiving features. The dental base can include different configurations each corresponding to one or more treatment steps. Dental aligners can be conveniently and inexpensively fabricated using the physical arch models at different treatment steps. The shared use of physical tooth models and the dental base between treatment steps significantly reduces the treatment time and cost. Various steps of the disclosed treatment system and methods are disclosed in the above referenced and commonly assigned U.S. patent applications, the disclosures of which are incorporated herein by reference.

Physical tooth models can be fabricated before the first treatment step or produced again in any of the subsequent steps if any of the tooth models are worn or damaged. A plurality of tooth models can also be fabricated at once to save set-up time and handling cost. In one example, the physical tooth models can be molded using the negative impression 280 in a casting chamber or the container 290. The container 290 can be filled with a malleable casting material. The container 290 can be sealed. The casting material is solidified with the assistance of heating, pressure, and/or UV irradiation. A physical arch model of the subject's arch can then be obtained by removing the solidified casting material. The physical arch model can then be separated into a plurality of tooth models. The one ore more reference marks 295 can be simultaneously molded on the physical arch model such that the surface points on the physical arch model can be accurately translated back to the original coordinates for the negative arch impression. Details of molding physical arch models are disclosed in the above referenced and commonly assigned U.S. patent application Ser. No. 11/013,160, titled "System and methods for casting physical tooth model" by Huafeng Wen, filed Dec. 14, 2004 and U.S. patent application Ser. No. 10/979,823, titled "Method and apparatus for manufacturing and constructing a physical dental arch model" by Huafeng Wen, filed Nov. 2, 2004, the disclosures of which are incorporated herein by reference.

FIG. 3A illustrates a subject's tooth 300 that includes a tooth body 310 and roots 320. In accordance with the present invention, the tooth movements can be decoupled into rotations around the roots 320 and translations of the roots 320. The translations of the roots 320 can be described by a coordinate system, such as a Cartesian coordinates defined by X-, Y-, and Z-axes. The longitudinal axis L of the tooth 300 can rotate along the polar direction P, the direction of self-rotation S, and the azimuthal direction A. Although alternative descriptions of movements exist, the disclosed definition of the teeth movement has the advantages of decoupling the large (rotational) movements from the small (translational) movements. Since the roots 320 are anchored down deep, the easiest movements of a tooth 300 under external forces are the rotations around the roots 320, whereas the translations of the roots 320 are of much smaller magnitudes. The roots of the tooth can be viewed as a pivot point about which the tooth rotates.

Figure 5:
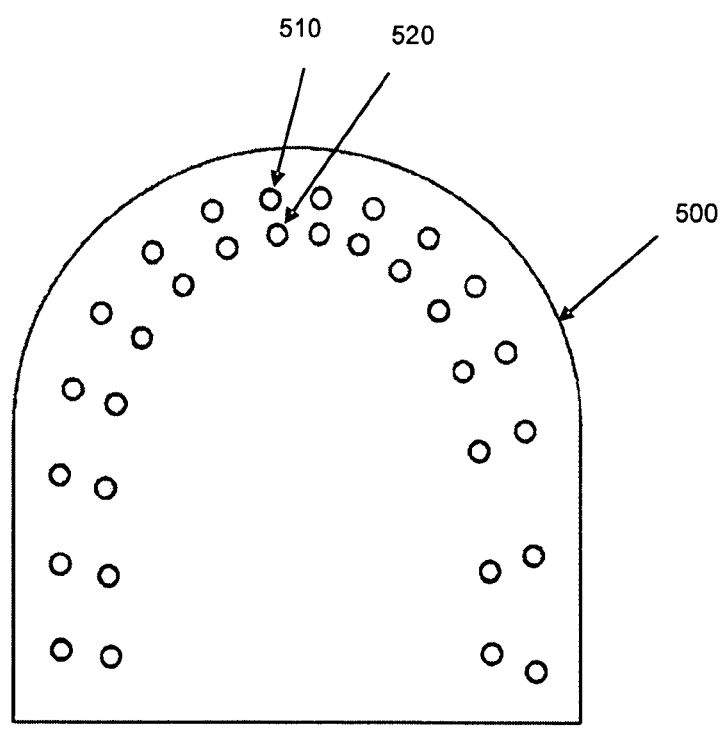
FIG. 5 is a top view of a dental base comprising a plurality of sockets for receiving pins affixed on the physical tooth models.
Figure 6:
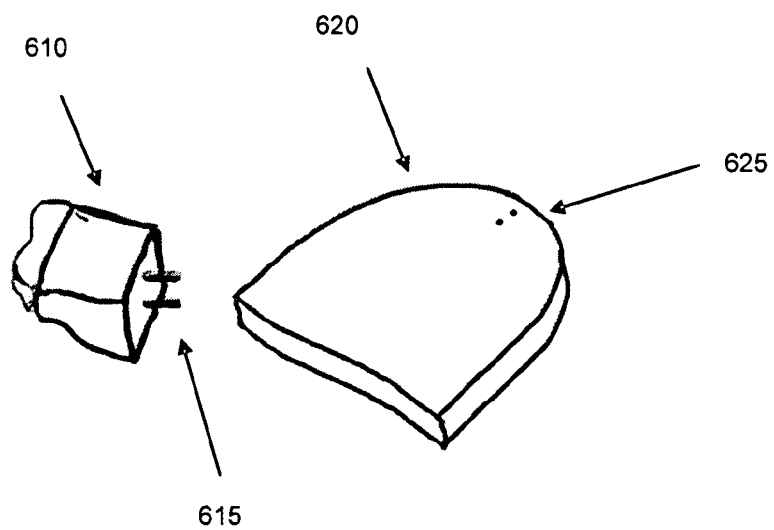
FIG. 6 illustrates a physical tooth model comprising two pins that allow the physical tooth model to be plugged into two corresponding sockets in a dental base.

FIG. 3B illustrates a tooth model 350 that can simulate the movements of the subject's tooth 300 in FIG. 3A. The tooth model 350 can include a tooth model body 360 and one or more registration features 370. The tooth model body 360 can simulate the tooth body 310. In accordance with the present invention, the registration features 370 can simulate the roots 320. The registration features 370 can include a pin, a protrusion, a stud, a socket, a slot, a hole, and other features that can be attached to the receiving features on the dental base as shown in FIGS. 5 and 6.

The simulation of the registration features 370 of the roots 320 can be assisted by a digital representation of the subject's tooth, that is, a digital tooth model. Images of the subject's teeth including the roots can be can be captured by X-ray in different directions. 3D digital models of the subject's teeth can be constructed from the images. The tooth model can also be scanned optically or measured by a location device to obtain a digital tooth model. The digital tooth model can be extrapolated to describe the roots of the tooth. The registration features 370 can then be simulated such that the ends of the registration features 370 are at the same locations relative to the tooth model 350 as the roots 320 relative to the tooth 300.

The movements of the tooth model 350 can be described by coordinate systems identical to those used for the subject's tooth 300 in FIG. 3A. The translation of the registration features 370 is described by a Cartesian coordinate system based on the X'-, Y'-, and Z'-axes. The rotation of the tooth model 350 can be described by the rotations of the longitudinal axis L' of the tooth model 350 along the polar direction P', the self-rotation direction S', and the azimuthal direction A'.

Figure 3C:
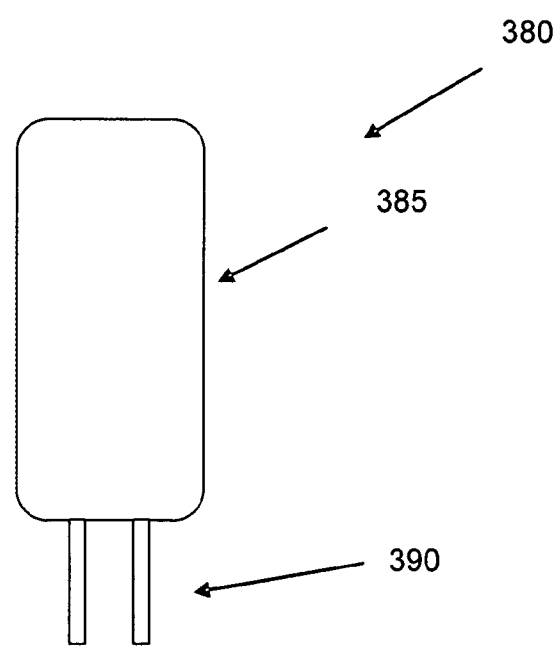
FIG. 3C illustrates a tooth model having registration features.

FIG. 3C shows a generalized tooth model 380, having a tooth body 380 and alignment pins (simulating roots) 390.

Dental aligner can be formed using the tooth models attached to the dental base at each step of the dental treatment. Because the registration features mimic the roots of the subject's teeth, the tooth models attached to the dental base can most closely simulate the present or the target configurations of the subject's teeth. The movements of the subject's teeth are decoupled to large movements (i.e. rotations around the registration features or the roots of the teeth) and small movements (i.e. translations of the registration features or the roots). The dental aligner can therefore focus on the large movements at each treatment step, which normally involves minimal translation of the roots. The dental aligner produced can therefore produce more accurate movement in the subject's teeth.

The disclosed dental aligners can also be more effective in moving subject's teeth. The prior art dental aligners often attempt to rotate the subject's teeth around point above the roots of the teeth, which often creates un-realistic or unwanted movements. The undesirable movements often have to be corrected in rework steps. The disclosed system can reduce the number corrective or rework treatment steps, thus minimizing the total number of treatment steps. The cost and time for the treatment are reduced.

The disclosed system and methods also simplifies the orthodontic treatment process compared to the prior art systems. The decoupling between rotations around the roots of the subject's teeth and the translation of the roots helps to focus the teeth movements on the primary movements, that is, the rotations around the roots of the teeth. In many cases, no or only minimal translational movements are required at the roots of the teeth.

As described above, constraining the movement of components of the dental arch (e.g., teeth) may also help in determining the intermediate digital (or physical) models interpolated from the initial model and the final (desired) dental arch configuration. In particular, constraining the movement of the teeth so that they more accurately model the movement of teeth whose roots are embedded within the gingiva and jaw is likely to result in more accurate and effective aligner designs. One way to achieve this is to constrain or limit movement in X-, Y- and/or Z-axes, while more readily allowing movement about the roots (e.g., azimuth and polar movement).

In other cases, a tooth can be constrained to rotate along just one or two of the polar, self-rotation, and the azimuthal directions in a particular treatment step. In other cases, the roots of a tooth can be constrained not to move in the X-, Y- or Z-directions in another treatment step. The constraints on the rotational movements help to reduce the variable degrees of freedom adjusting teeth configurations, which simplifies treatment designs.

In one aspect, the constrained teeth movement reduces the probability of interference between neighboring teeth. Details of designing teeth movement without interference between adjacent teeth are disclosed in the commonly assigned and above referenced U.S. patent application Ser. No. 11/013,156, titled "Producing non-interfering tooth models on a base" by Huafeng Wen, there content of which is incorporated herein by reference.

In another aspect, different constrained tooth movement at different treatment steps makes it easier to monitor the teeth movement over the treatment process. The treatment can be more focused and the teeth can be moved more directly to the final configuration of the treatment plan. The simplified teeth movement also reduces the chance for incorrect movement and thus reduces the corrective measures in the treatment. The number of treatment steps can be reduced as a result, which decreases the cost and time spent.

Figure 4:
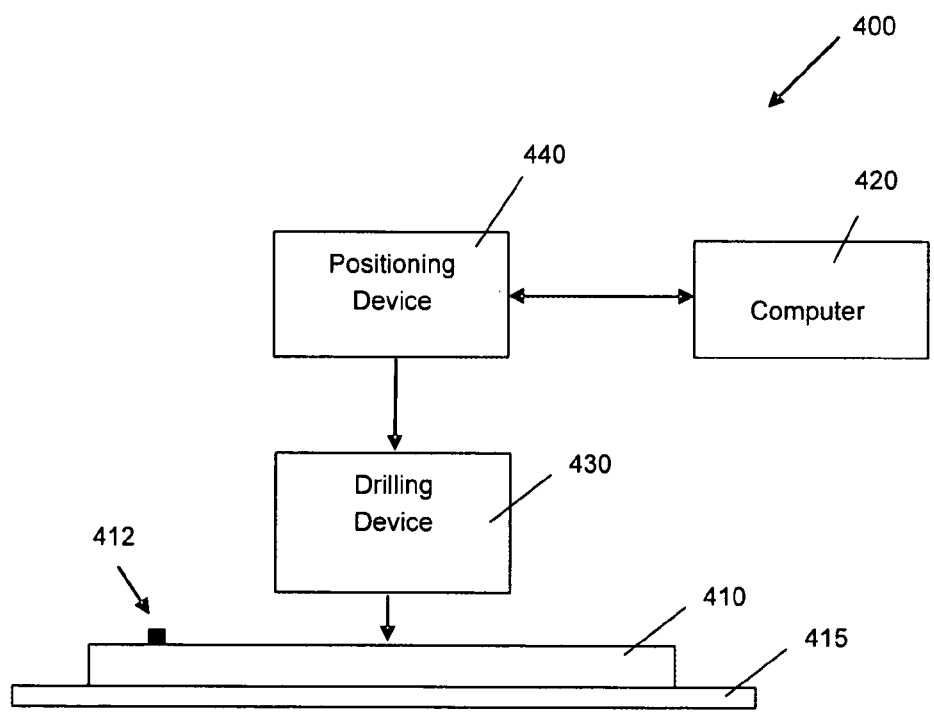
FIG. 4 illustrates a system for producing receiving features on a dental base for receiving physical tooth models.

The registration features 370 can be simultaneously produced in the molding process by molding them into the malleable casting materials. For examples, the registration features 370 can be pins that are inserted into the malleable casting material before it is solidified. Alternatively, the registration features 370 can be produced in the tooth model 350 after the making of the physical arch model and before the physical arch model is separated into tooth models 350. For example, the registration features 370 can include sockets that can be drilled by a drilling system 400 on the physical arch model as shown in FIG. 4. Details of obtaining a physical dental arch model having registration features and 3D reference positions are disclosed in above referenced US patent application titled "Producing a base for accurately receiving dental tooth models" by Huafeng Wen, filed Dec. 14, 2004, the content of which is incorporated herein by reference.

The tooth model 350 shown in FIG. 3B can include a tooth model body 360 and one or more registration features 370. The registration features 370 can include a pin, a protrusion, a stud, a socket, a slot, a hole, and other features that can be attached to the receiving features on the dental base as shown in FIGS. 5 and 6. The registration features can be simultaneously produced in the molding process by molding them into the malleable casting materials in step 185. For examples, registration features that are pins can be inserted into the casting material before it is solidified. Alternatively, the registration features 370 can be produced in the tooth model 350 after the making of the physical arch model and before the physical arch model is separated into tooth models 350. For example, the registration features 370 can include sockets that can be drilled by a drilling system 400 on the physical arch model as shown in FIG. 4. Details of obtaining a physical dental arch model having registration features and 3D reference positions are disclosed in above referenced US patent application titled "Producing a base for accurately receiving dental tooth models" by Huafeng Wen, filed Dec. 14, 2004, the content of which is incorporated herein by reference.

Receiving features for receiving the registration features in the tooth model are next produced on a dental base in step 186. The receiving features on the dental base are complimentary to and compatible with the registration features on the tooth models. The receiving features can include one or more of pins, protrusions, studs, sockets, slots, and holes. As shown in FIG. 4, the dental base 410 is held to a stage 415. A drilling device 430 is mounted on a positioning system 440 that can move the drilling device 430 in three dimensions. The positioning system 440 first locates the reference points 412 on the dental base 410 under the control of a computer 420. The reference points 412 precisely correspond to the reference marks 295 in the dental impression 280. The positioning system 440 can define a coordinate system based on the reference points on the dental base 410. The coordinates of the dental base 410 can be quantitatively translated to the original coordinates of the negative dental impression 280 using the reference marks 295. The computer 420 stores the locations of the sockets to be made on the dental base 410. The locations of the sockets correspond to the registration features 370 (pins) on the tooth model 350. Both the sockets and the registration features 370 can be defined by the original reference marks 295. For example, the locations of the receiving features on the dental base can depend on at least two factors: first, the measured positions of the subject's teeth after the teeth movement caused by the last dental aligner; and second, the desired positions of the subject's teeth.

The positional system 440 moves the drilling device 430 to the intended locations for the sockets stored in the computer 420. Drilling device 430 can drill the sockets using a mechanical drill bit or by burning to form them with any appropriate device, such as a high-power laser beam.

Alternatively, the dental base 410 rather than the drilling device 430 can be mounted on a positioning device. The positioning device is capable of producing relative movement between the dental base 410 and the drilling device 430. A coordinate system is developed based on the reference points 412 that can be quantitatively translated to the coordinate system based the reference marks 295 on the dental impression 280. The dental base 410 is moved to positions to allow the sockets to be drilled at the intended locations. The precise registration between the teeth positions on the dental base 410 assures the tooth models 350 accurately mounted on the dental base 410 as specified by the desired positions (or the target configurations) of the teeth for the next treatment step.

FIG. 5 is a top view of a dental base 500 comprising a plurality of sockets 510 and 520 for receiving the studs of a plurality of tooth models. The positions of the sockets 510,520 are determined by either the initial teeth positions in a subject's arch or the teeth positions during the orthodontic treatment process. The base 500 can be in the form of a plate as shown in FIG. 5, comprising a plurality of pairs of sockets 510,520. Each pair of sockets 510,520 is adapted to receive two pins associated with a physical tooth model. Each pair of sockets includes a socket 510 on the inside of the tooth arch model and a socket 520 on the outside of the tooth arch model.

FIG. 6 shows a tooth model 610 affixed with two pins 615. A dental base 620 includes sockets 625 that can be in registration with the pins 615. The sockets 625 are adapted to receive the two pins 615 to allow the tooth model 610 to be assembled with the dental base 620. Since the sockets 625 and the pins 615 are fabricated based on the same coordinate system. They can be in precise registration to allow they to be assembled together. The tooth models 610 are assembled onto the dental base 620 to form a dental arch model in step 187.

Figure 7:
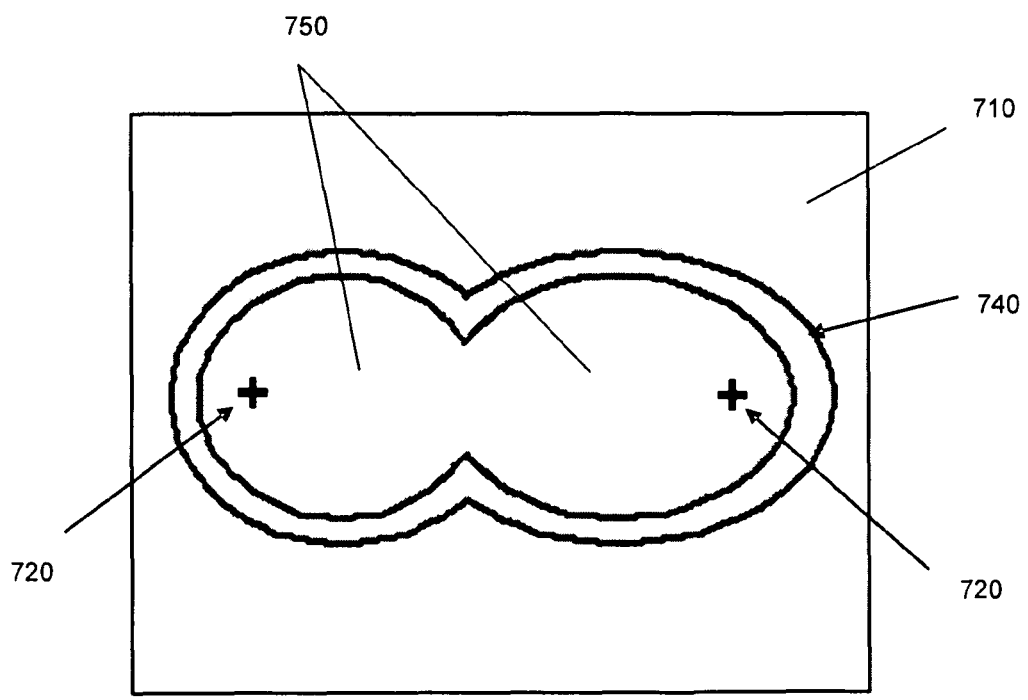
FIG. 7 illustrates an arrangement of fabricating a dental aligner using a dental arch model.

A dental aligner can be conveniently fabricated using the dental arch model in step 188. FIG. 7 illustrates an arrangement of fabricating a dental aligner using a dental arch model. A sheet 710 of aligner-making material is attached to a sheet holder and then lifted up near a heating element. The sheet can be made of uniform distribution of a single material or comprise multiple layers of different materials. After the aligner-making material is heated by a specified time, the sheet holder is pressed on the subject's dental arch model on the base plate. A vacuum pump removes air at the bottom of the base plate to cause the softened aligner making material to relax and fittingly form around the surface the subject's dental arch model. This process of aligner making is referred to as the vacuum forming.

The subject's dental arch model can include registration points 412 that can be copied onto the sheet 710 of aligner-making material during vacuum forming. The copied registration marks 720 are formed on the aligner 750. A digital arch model captures the shape information of the subject's tooth models and the information about the registration marks. The digital arch model can further specify the location of the features to be produced on the subject's teeth to receive the through holes that can allow the dental aligner to be snapped onto the subject's teeth.

An aligner obtained as described herein may be specifically designed to move the subject's teeth at the current stage of the treatment process toward the desired positions. The aligner is to be worn by the subject in step 160. The process from step 160 to step 180 can be repeated.

The physical tooth models and the dental base can be shared between different treatment steps. Physical arch models can be configured and re-configured for different treatment steps. Dental aligners can be conveniently and inexpensively fabricated using the physical arch model.

Example 2: Manual Determination of Movement Path and Intermediate Target Configurations In one variation, the method of producing removable orthodontic appliances (aligners) relies upon a technician to initially set the intermediate target configurations (treatment steps). The aligners are made of clear plastic and are molded to fit snugly over a subject's teeth, as described above.

Overall, the treatment system includes a series of aligners, each of which has a configuration that differs slightly from the untreated position of the subject's teeth. Each aligner exerts pressure upon the subject's teeth, forcing the teeth to conform to the configuration of the aligner. When the subject's teeth have conformed to the configuration of a particular aligner, the subject moves on to a new aligner. In general, the treatment process is finished when the subject's teeth have reached the configuration desired by the treating clinician.

Figure 1B:
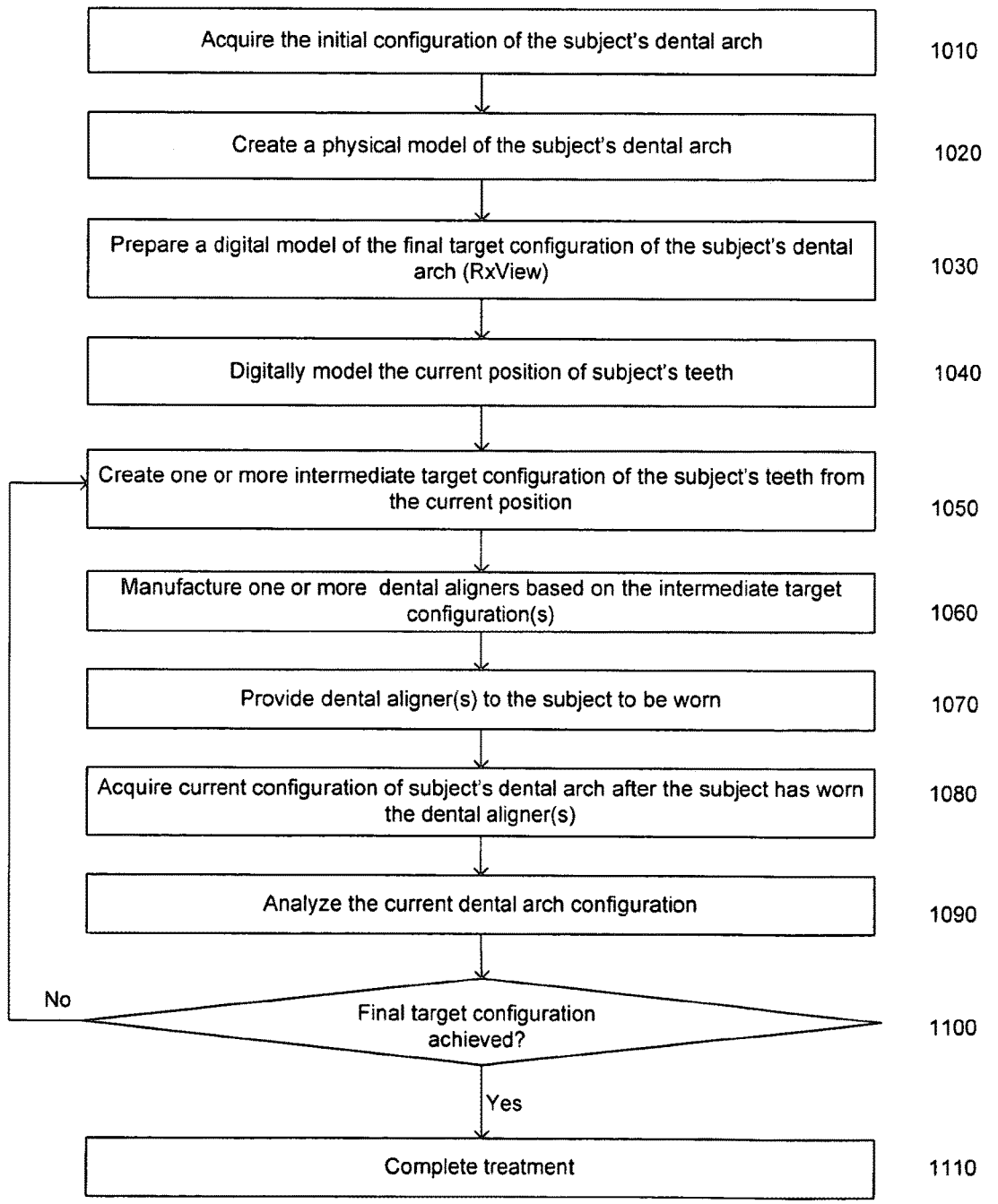
FIG. 1B is a flow chart showing another variation of the dental treatment method having feedback as described herein.

FIG. 1B illustrates the steps followed by one variation of this treatment method. The manufacturing process begins with subject information provided by practitioner 1010. This information is collected by the practitioner, through his examination of a subject, and includes dental impressions of the subject's upper and lower teeth, a "wax bite" (i.e., an impression of the subject's teeth that the subject creates by biting into a piece of wax), x-rays of the subject's teeth, photographs of the subject's face, and a prescription. The manufacturing entity uses this information to manufacture the aligners customized for each subject.

A physical model of the subject's teeth is created from the provided information by the manufacturing entity 1020. The dental impressions and x-rays of the subject's teeth are used to create a physical model of the subject's teeth. This creation of a physical model is accomplished through the following steps. First, a technician reviews the dental impressions and x-rays to determine the orientation of each of the subject's teeth. By looking at the dental impressions and x-rays, the technician is able to determine the z-axis of each tooth, i.e., the direction in which the tooth points. This "z-axis" information is input into a three dimensional digitizer. As described above, a three dimensional digitizer is a spatial measuring tool used to determine the x, y and z coordinates of points on the surface of an object. In this case, the three dimensional digitizer is used to determine the x, y and z coordinates of points on the surface of the subject's dental impressions. The "z-axis" information is typically calculated by using a 3D digitizer, (e.g., a MicroScribe) to obtain several coordinates on the crown. These coordinates are then used to estimate the positions of the roots of each individual tooth of the subject.

Next, a computer numerical controlled (CNC) milling machine is used to drill a series of holes, which correspond to the estimated root positions, into a plastic plate, (base plate). Two holes are drilled for each tooth and a pin is inserted into each hole. The length of each pin is greater than the depth of each hole, such that, once inserted, each pin partially protrudes from the base plate. Two base plates are created-one for the subject's upper arch and one for the subject's lower arch.

Modeling material is next poured into the subject's dental impressions and the base plates are mated to the dental impressions so that the pins, protruding from the base plates, protrude into the liquid modeling material. As the modeling material hardens, the pins become embedded in the material, creating a model of the teeth with two pins protruding from each tooth. The models of the teeth, including the pins, are removed from the dental impressions and base plates. Finally, these models are then separated, i.e., cut apart to create individual models of each of the subject's teeth.

A digital image of the subject's teeth (a digital model) is then produced to help guide the treatment formulation 1030. The models of the subject's teeth, the estimated positions of the roots of the subject's teeth, and the practitioner's prescription are used to create a digital image of the prescribed position of the subject's teeth. This process is accomplished through the following steps. First, the models of each of the subject's teeth are mounted onto another base plate, referred to as a "scanning plate," one at a time (or in some variations, in a group). The scanning plate may be made of the same kind of material as the base plate used in the modeling process described above, but is given a different name to indicate that it is used at a different point in the process and for a different purpose.

The model of each tooth, once mounted onto the scanning plate, is scanned using a laser to obtain data representing its three dimensional geometry. These data, combined with the estimated root positions and the practitioner's prescription, are used to create a digital image of the prescribed position of the subject's teeth, i.e., an image of the subject's teeth positioned in accordance with the practitioner's prescription. This digital image is referred to as the "PrescriptionView Image" or RxView. The PrescritionView is a computer graphic image encoded in a data format. The data contained in the PrescriptionView Image is adequate to create a visual representation of the subject's teeth, however, by itself it may not be adequate to provide a basis for the manufacture of physical aligners.

The PrescriptionView is typically an image of the entirety of the subject's teeth, including the portion of the teeth below the gum line. The PrescriptionView of the portion of the teeth above the gum line is created using the data obtained from the laser scan of the model teeth. The PrescriptionView of the portion of the teeth below the gum line is an approximation based on the type of tooth represented—for example, the image of a molar is based on the shape of a molar and the image of a bicuspid is based on the shape of a bicuspid. The PrescriptionView may be provided to the practitioner via computer for approval. The practitioner examines the PrescriptionView using a computer program known, allowing the practitioner to submit instructions and treatment modifications. Once the practitioner has viewed the PrescriptionView, the practitioner may either approve the PrescriptionView or modify the PrescriptionView.

After the practitioner determines that an acceptable PrescriptionView has been created, a technician (e.g., part of the manufacturing entity) begins producing the aligners individually, for shipment of two sets at a time. A "set" of aligners includes an aligner for the subject's top teeth and an aligner for the subject's bottom teeth, unless the subject seeks treatment for his top or bottom teeth, exclusively, in which case his "set" of aligners will consist of a single aligner.

The physical manufacture of the aligners may utilize a third computer program that uses the data obtained from the laser scan of the individual model teeth and the estimated positions of the roots of the subject's teeth to create a digital image of the current position of the subject's teeth 1040. A technician then looks at this digital image and, using the software, manually adjusts the positions of the teeth to a first-modified position 1050. The technician generally relies upon judgment and experience to manually adjust the positions of the teeth using the software, so that the movement necessary to change the position of a tooth from the current position to the first-modified position can be achieved using a single aligner. In making this adjustment, the technician may refer to the PrescriptionView as a visual guide only, much as a lab technician would look at a physical model of teeth as a guide. Data from the PrescriptionView does not need to be used in modeling these intermediate treatment steps (intermediate target configurations of the teeth). In some variations, the software used to model these intermediate target configurations may apply the constraints to the technician's ability to move the teeth. For example, the technician may be limited in how far he or she can move a tooth in rotation about the roots, or translate the teeth in x-, y- or z-directions, as described above. The software used by the technician to model the intermediate target configurations may also protect against technician error by limiting the range of movement allowed each tooth. For example, it may prohibit the technician from positioning the teeth in undesirable or impossible orientations, e.g., overlapping orientations.

Once this adjustment is complete, a dental aligner is manufactured from the first intermediate target configuration (the "first modified position" described above) 1060. A computer numerical controlled (CNC) milling machine is used to drill a series of holes, corresponding to the "first-modified" root positions, into a base plate referred to as a "staging plate." The staging plate is identical to the casting and scanning plates described above, but is given a different name to indicate that it is used at a different point in the process. The technician inserts each physical tooth model into its corresponding pair of holes in the "first-modified" staging plate. This creates a physical model of the first-modified target position of the subject's teeth. The technician then creates an aligner by thermoforming a polymer shell over this physical model.

In some variations, a second-modified target position (e.g., a second intermediate target configuration) may be generated immediately from which a second aligner may be produced. The technician looks at the digital image of the first-modified position with the software and, using his judgment and experience, manually adjusts the first-modified position to a second-modified position, as described above. A computer numerical controlled (CNC) milling machine is then used to drill a series of holes, corresponding to the "second-modified" target root positions, into a staging plate. The technician inserts the model teeth into the new staging plate holes, and a second aligner is molded over the physical model.

Typically two aligners may be fabricated at a time, spanning six weeks of treatment, and provided to the subject direction, or to the practitioner to provide to the subject to be worn 1070. These aligners may be worn, for example, for 21 days. Two sets of aligners are sent to a practitioner at one time. The time during which the subject wears these two sets of aligners, 42 days (.about.6 weeks) is referred to as the "treatment period." After two sets of aligners are provided to the practitioner, the practitioner receives a message inquiring whether the practitioner would like to make adjustments to the treatment, consult with technician, or have the technician design and manufacture two more aligners.

As the stages of treatment progress, the practitioner may view the newly modified teeth positions and provides feedback and input to the technician, changing the treatment pathway (e.g., the course of the treatment) as the subject progresses from aligner to aligner. Subsequent aligners can be created by repeating this process, with continuing practitioner input and modification as treatment progresses.

The practitioner has the ability to make adjustments to the next two sets of aligners for approximately four weeks after the start of each treatment period (leaving two weeks during which the next two sets of aligners can be manufactured). This interactive process ensures that each pair of aligners can provide repositioning based on the current state of the subject's teeth, as examined by the clinician.

As described herein, the actual movement of the dental arch (teeth) may be feed back into the treatment. For example, the position of the teeth after the subject has worn one or more aligners may be used to plan the next (or next few) treatment steps. In some variations, the practitioner provides information about the configuration of the subject's teeth after the subject has worn one or more dental aligners to the technician (manufacturer) 1080. The manufacturer (or the practitioner) may determine the change in position for individual teeth 1090, and may adjust the next target configuration accordingly 1050. If one or more teeth is proving particularly resistant to movement, the practitioner may increase the amount of force applied to that tooth by the next aligner(s) or may change the way that the tooth is being moved by the aligner. In some variations, the actual position of the subject's teeth after wearing the most recent aligner can serve as the actual starting point for determining the next target configuration, rather than using the previously determined intended target configuration, as described above.

In this example, the aligners are shipped to the practitioner two sets at a time, with the packaging being designed to allow the clinician to select the proper set to give the subject without the necessity of placing marks or instructions on the aligners. For example, each set is packaged individually and the packages are stacked one on top of the other, such that the top set must be removed first, leaving the bottom set intact and attached to the package, to be used during the second half of the treatment period. The manufacturer can continue to fabricate and deliver aligners until the practitioner informs them that treatment is complete.

In some variations of the aligners, buttons may be used in conjunction with the treatment. Buttons are small structures that are physically bonded to a subject's teeth. Aligners can be manufactured such that they include "windows," i.e., holes through which these buttons protrude. When aligners with windows are fitted onto teeth with buttons, the aligners can exert additional or different forces upon selected teeth allowing for more aggressive or more specialized tooth movement. The practitioner may indicate whether the subject requires buttons and, if so, the prescription indicates where the buttons should be positioned. Based upon this prescription, the manufacturer creates a template, which the practitioner uses to attach, i.e. glue, the buttons to the subject's teeth.

Thus, in the example provided above, the intermediate target positions of a subject's teeth are determined using a technician's judgment and experience, and are not determined by any mathematical algorithm or formula. However, it should be clear that in forming the intermediate target positions, the technician may be guided or assisted by software which assists in both modeling the movement of teeth (e.g., reflecting realistic interaction between teeth and difficulty to move in certain directions, etc.).

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

All of the references provided herein are incorporated by reference in their entirety for all reasonable purposes, and their disclosures are intended to be considered part of the full disclosure.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What we claim is:

1. A non-transitory computer readable storage medium having stored thereon, computer-executable instructions that, when executed by a computer, cause said computer to perform a method for treating a subject's teeth, comprising:
   simultaneously presenting, in a same directional view, a first digital representation at a first display window and a second digital representation at a second display window, wherein said first digital representation comprises one of a pre-modified tooth arch of a patient and a post-modified tooth arch of said patient, and wherein said second digital representation comprises the other of said pre-modified tooth arch and said post-modified tooth arch;
   in response to a receipt of tooth rotation instructions, executing a first rotation, wherein said executing said first rotation comprises:
   rotating said first digital representation presented at said first display window; and
   simultaneously with said executing said first rotation, executing a second rotation, wherein said executing said second rotation comprises:
   rotating said second digital representation presented at said second display window, wherein said first rotation and said second rotation are executed in a same direction and in a same amount.

2. The non-transitory computer readable storage medium of claim 1, further comprising:
   providing selectable directional view icons that, upon selection, communicate a directional view by which said first digital representation and said second digital representation will be viewed.

3. The non-transitory computer readable storage medium of claim 1, further comprising:
   detecting a potential collision of adjacent teeth within said post-modified tooth arch.

4. The non-transitory computer readable storage medium of claim 1, further comprising:
   detecting a potential collision of a root of a first tooth with a root of a second tooth of said post-modified tooth arch, wherein said second tooth is adjacent to said first tooth.

5. The non-transitory computer readable storage medium of claim 3, further comprising:
   providing an alert that said potential collision may occur.

6. The non-transitory computer readable storage medium of claim 3, further comprising:
   based on said potential collision, not allowing a tooth of said post-modified tooth arch to be digitally rotated such that a collision representing said potential collision is realized.

7. The non-transitory computer readable storage medium of claim 1, further comprising:
   representing each tooth of said pre-modified tooth arch and said post-modified tooth arch as a mesh of points, such that an overlapping of said mesh of points indicates that a potential collision between adjacent teeth has occurred.

8. The non-transitory computer readable storage medium of claim 1, further comprising:
   using boundary parameters to prevent an over-rotation of said post-modified tooth arch, such that an amount of rotation and displacement is prescribed for each tooth of said pre-modified tooth arch.

9. The non-transitory computer readable storage medium of claim 1, further comprising:
   determine a movement pathway based on said pre-modified tooth arch and said post-modified tooth arch.

10. A non-transitory computer readable storage medium having stored thereon, computer-executable instructions that, when executed by a computer, cause said computer to perform a method for treating a subject's teeth, comprising:
   simultaneously presenting, in a same directional view, a first digital representation at a first display window and a second digital representation at a second display window, wherein said first digital representation comprises a one of a pre-modified tooth arch of a patient and a post-modified tooth arch of said patient, and wherein said second digital representation comprises the other of said pre-modified tooth arch and said post-modified tooth arch, wherein digital representations of said pre-modified tooth arch and said post-modified tooth arch comprise a display of roots of each tooth therein;
   in response to a receipt of tooth rotation instructions, executing a first rotation, wherein said executing said first rotation comprises:
      rotating said first digital representation presented at said first display window; and
   simultaneously with said executing said first rotation, executing a second rotation, wherein said executing said second rotation comprises:
      rotating said second digital representation presented at said second display window, wherein said first rotation and said second rotation are executed in a same direction and in a same amount.

\* \* \* \* \*